US012810513B2

(12) United States Patent
Kobayashi et al.

(10) Patent No.: US 12,810,513 B2
(45) Date of Patent: Nov. 24, 2026

(54) MEDICAL IMAGE PROCESSING APPARATUS, MEDICAL IMAGE PROCESSING METHOD, AND X-RAY DIAGNOSTIC APPARATUS

(71) Applicant: Canon Kabushiki Kaisha, Tokyo (JP)

(72) Inventors: Yoshimasa Kobayashi, Nasushiobara (JP); Daisuke Sato, Utsunomiya (JP); Tomio Maehama, Nasushiobara (JP); Risa Hayashi, Utsunomiya (JP); Tamotsu Ino, Yaita (JP); Katsunori Kojima, Hadano (JP); Yoshinori Saito, Otawara (JP); Naoto Watanabe, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 439 days.

(21) Appl. No.: 18/454,190

(22) Filed: Aug. 23, 2023

(65) Prior Publication Data

US 2024/0070937 A1 Feb. 29, 2024

(30) Foreign Application Priority Data

Aug. 31, 2022 (JP) ................................. 2022-138450

(51) Int. Cl.
*G06T 12/20* (2026.01)
*A61B 6/02* (2006.01)

(52) U.S. Cl.
CPC .............. *G06T 12/20* (2026.01); *A61B 6/025* (2013.01); *G06T 2200/28* (2013.01); *G06T 2207/10048* (2013.01)

(58) Field of Classification Search
CPC ..... A61B 6/025; G06T 11/06; G06T 2200/28; G06T 2207/10048
See application file for complete search history.

(56) References Cited

U.S. PATENT DOCUMENTS

| | | | | |
|---|---|---|---|---|
| 5,694,476 | A * | 12/1997 | Klippel .................... | H04R 3/02 381/59 |
| 6,528,793 | B1 * | 3/2003 | Chen ........................ | G01V 5/20 250/363.02 |

(Continued)

FOREIGN PATENT DOCUMENTS

| | | |
|---|---|---|
| JP | 2017-26422 A | 2/2017 |
| WO | WO 2020/050107 A1 | 3/2020 |

OTHER PUBLICATIONS

Rautela et al., "Dual-modality synthetic mammogram construction for breast lesion detection using U-DARTS", Aug. 29, 2022, Biocybernetics and Biomedical Engineering, 42(3), 1041-1050 (Year: 2022).*

*Primary Examiner* — Blake C Riddick

(74) *Attorney, Agent, or Firm* — Oblon, McClelland, Maier & Neustadt, L.L.P.

(57) ABSTRACT

According to one embodiment, a medical image processing apparatus includes processing circuitry. The processing circuitry is configured to acquire three-dimensional thermographic image data by imaging a subject irradiated with infrared rays. The processing circuitry is configured to acquire a plurality of items of projection data by imaging the subject with tomosynthesis. The processing circuitry is configured to execute reconstruction based on the plurality of items of projection data and the three-dimensional thermographic image data.

15 Claims, 16 Drawing Sheets

(56) References Cited

U.S. PATENT DOCUMENTS

| | | | | |
|---|---|---|---|---|
| 2007/0110293 | A1* | 5/2007 | Arnon | G06V 10/147 382/128 |
| 2007/0213617 | A1* | 9/2007 | Berman | A61B 5/0091 600/473 |
| 2007/0224169 | A1* | 9/2007 | Sliwa | A61K 9/0009 424/93.2 |
| 2008/0219534 | A1* | 9/2008 | Faul | A61B 6/5235 382/131 |
| 2008/0260091 | A1* | 10/2008 | Maschke | A61B 1/00009 378/4 |
| 2009/0037130 | A1* | 2/2009 | Feiweier | A61B 90/36 702/104 |
| 2009/0259139 | A1* | 10/2009 | Stepien | A61B 10/0041 600/549 |
| 2010/0041998 | A1* | 2/2010 | Postel | A61B 5/015 600/475 |
| 2011/0191767 | A1* | 8/2011 | Pinsky | G16Z 99/00 717/176 |
| 2011/0191821 | A1* | 8/2011 | Pinsky | G16H 40/63 726/3 |
| 2011/0191822 | A1* | 8/2011 | Pinsky | G06F 15/16 726/3 |
| 2013/0148908 | A1* | 6/2013 | Barkan | G06T 5/50 382/239 |
| 2015/0257651 | A1* | 9/2015 | Angott | A61B 5/418 600/474 |
| 2017/0186192 | A1* | 6/2017 | Yang | G06T 11/003 |
| 2017/0301114 | A1* | 10/2017 | Yang | G06T 11/005 |
| 2018/0047555 | A1* | 2/2018 | Pringle | A61B 90/13 |
| 2018/0357762 | A1* | 12/2018 | Kobayashi | A61B 6/025 |
| 2019/0180488 | A1* | 6/2019 | Hoernig | G06T 7/70 |
| 2019/0385308 | A1* | 12/2019 | Kandlikar | A61B 5/4312 |
| 2020/0118308 | A1* | 4/2020 | Nakanishi | A61B 6/032 |
| 2020/0159313 | A1* | 5/2020 | Gibby | A61B 90/36 |
| 2020/0257812 | A1* | 8/2020 | Gibby | G06F 21/602 |
| 2020/0285902 | A1* | 9/2020 | Kobayashi | G06V 10/764 |
| 2020/0372693 | A1* | 11/2020 | Kobayashi | A61B 6/466 |
| 2021/0082092 | A1* | 3/2021 | Sargent | G06T 5/50 |
| 2021/0100521 | A1* | 4/2021 | Iwai | A61B 6/547 |
| 2021/0174938 | A1* | 6/2021 | Park | G16H 30/40 |
| 2021/0223855 | A1* | 7/2021 | Gibby | G06F 3/011 |
| 2022/0189062 | A1* | 6/2022 | Seo | G06T 15/20 |
| 2022/0202493 | A1* | 6/2022 | Gibby | A61B 34/10 |
| 2022/0254006 | A1* | 8/2022 | Jin | G06V 10/82 |
| 2022/0401042 | A1* | 12/2022 | Yamakawa | G06T 11/008 |
| 2023/0092496 | A1* | 3/2023 | Tang | A61B 6/035 378/19 |

* cited by examiner

MEDICAL IMAGE PROCESSING APPARATUS, MEDICAL IMAGE PROCESSING METHOD, AND X-RAY DIAGNOSTIC APPARATUS

CROSS-REFERENCE TO RELATED APPLICATION

This application is based upon and claims the benefit of priority from prior Japanese Patent Application No. 2022-138450, filed Aug. 31, 2022, the entire contents of which are incorporated herein by reference.

FIELD

Embodiments described herein relate generally to a medical image processing apparatus, a medical image processing method, and an X-ray diagnostic apparatus.

BACKGROUND

Tomosynthesis imaging is used to reduce an overlap of subjects in an X-ray diagnostic apparatus such as a mammographic apparatus, an X-ray fluoroscopic apparatus, and a general X-ray imaging apparatus. In tomosynthesis imaging, three-dimensional images are obtained by performing X-ray irradiation from various angles in a limited range, and reconstructing a plurality of items of projection data obtained by the irradiation.

In such tomosynthesis imaging, X-ray irradiation is performed from a limited range of irradiation angles. The range of irradiation angles of a mammographic apparatus is, for example, ±7.5, and is at most ±25 degrees, which is provided by a manufacturer that adopts a wide irradiation angle. To increase the resolution in the depth direction, the range of irradiation angles should be widened to gain a deeper view. If, for example, the currently adopted range of angles is ±7.5 degrees, it should be changed to a wider range of angles. However, increasing the range of irradiation angles leads to an increase in both the exposure dose and the tomosynthesis data collection time.

DETAILED DESCRIPTION

In general, according to one embodiment, a medical image processing apparatus includes processing circuitry. The processing circuitry is configured to acquire three-dimensional thermographic image data by imaging a subject irradiated with infrared rays. The processing circuitry is configured to acquire a plurality of items of projection data by imaging the subject with tomosynthesis. The processing circuitry is configured to execute reconstruction based on the plurality of items of projection data and the three-dimensional thermographic image data.

Hereinafter, an X-ray diagnostic apparatus including a medical image processing apparatus according to each of the embodiments will be described with reference to the accompanying drawings. In the description that follows, a case will be discussed as an example where the X-ray diagnostic apparatus is a mammographic apparatus; however, the configuration is not limited thereto. For example, a given X-ray apparatus configured to perform tomosynthesis imaging, such as an X-ray fluoroscopic apparatus and a general X-ray imaging apparatus, can be used as the X-ray diagnostic apparatus.

First Embodiment

Figure 1:
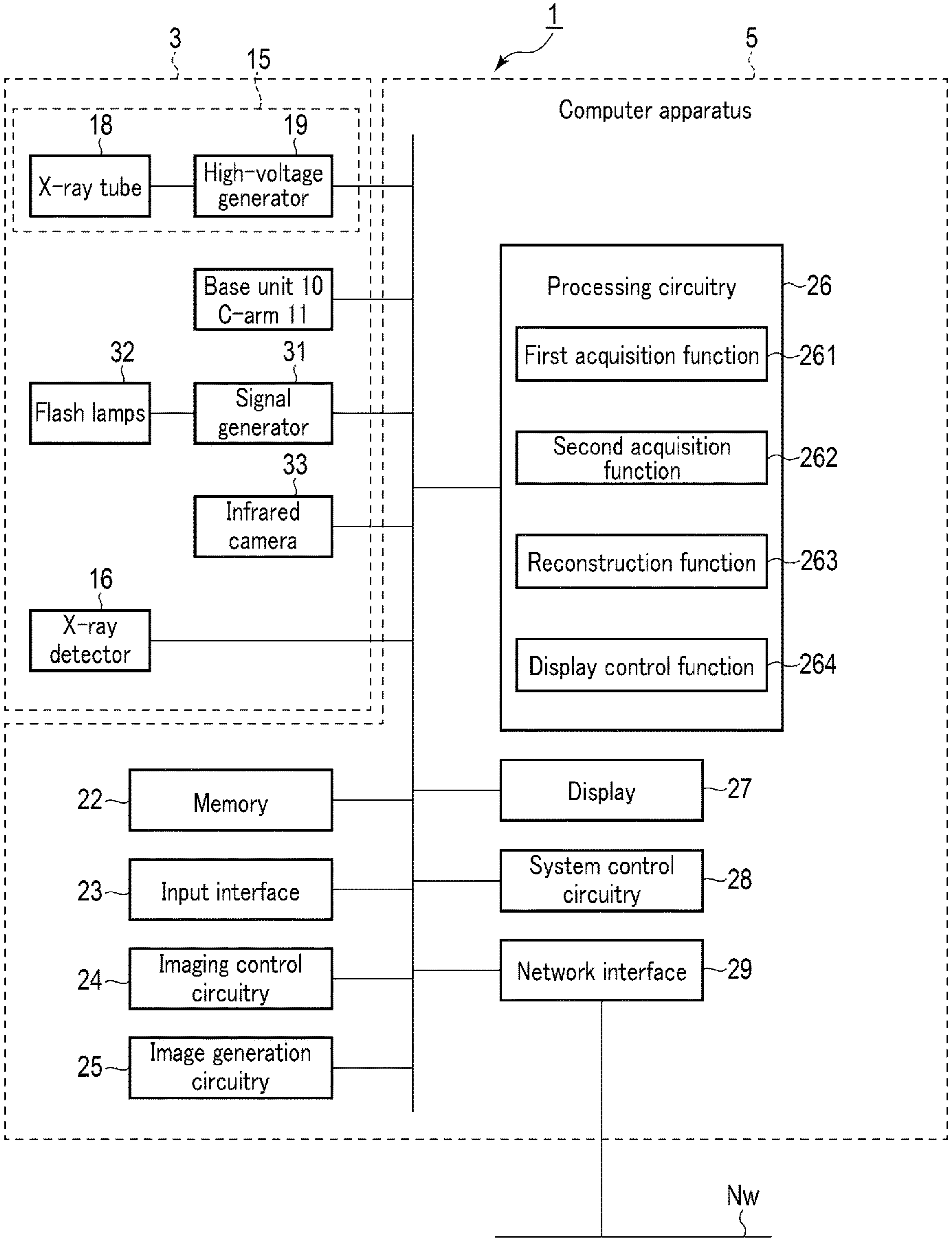
FIG. 1 is a block diagram showing a configuration example of an X-ray diagnostic apparatus according to a first embodiment.
Figure 2:
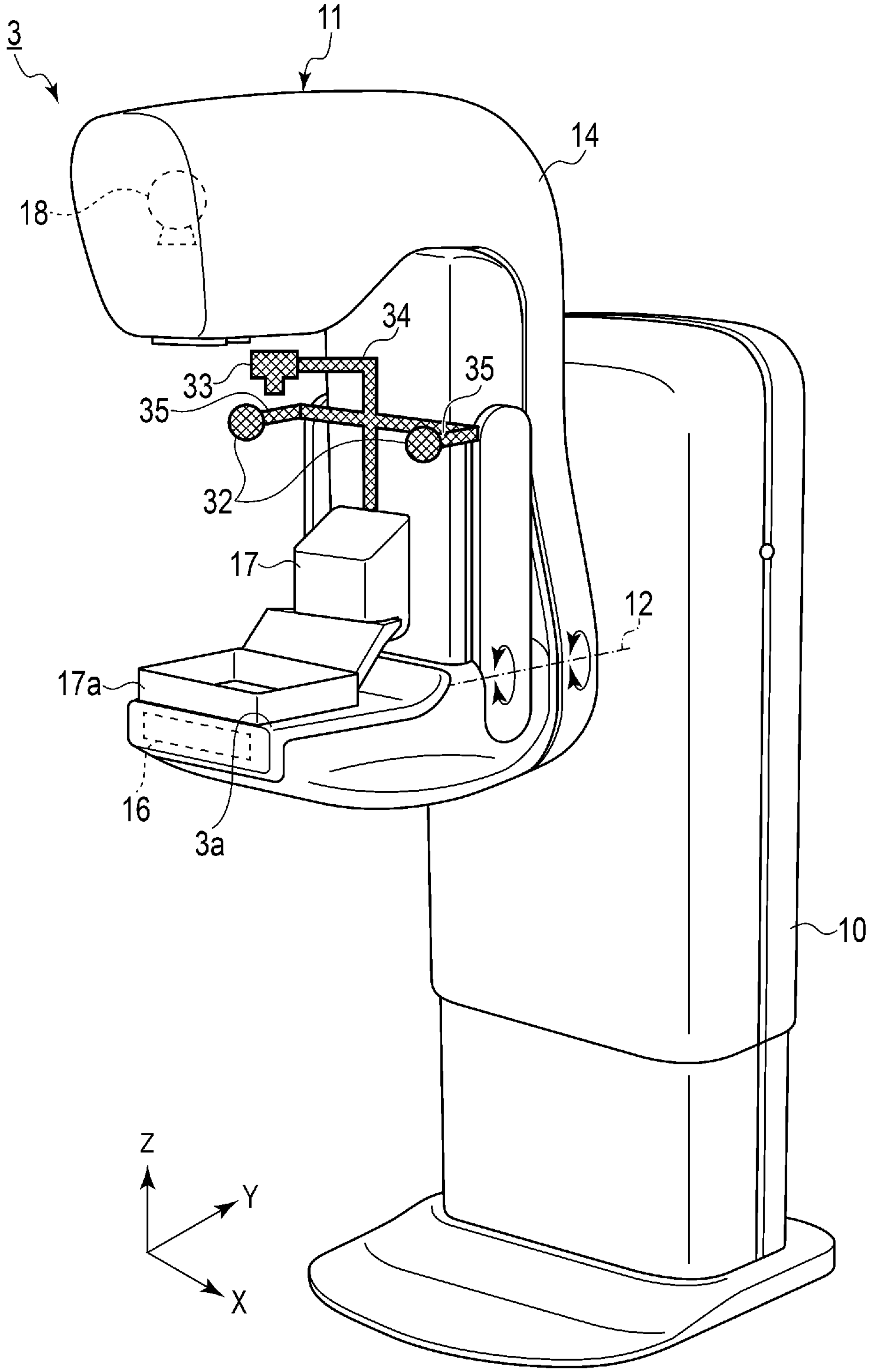
FIG. 2 is a perspective view showing an example of an outer appearance of X-ray imaging equipment according to the first embodiment.
Figure 3:
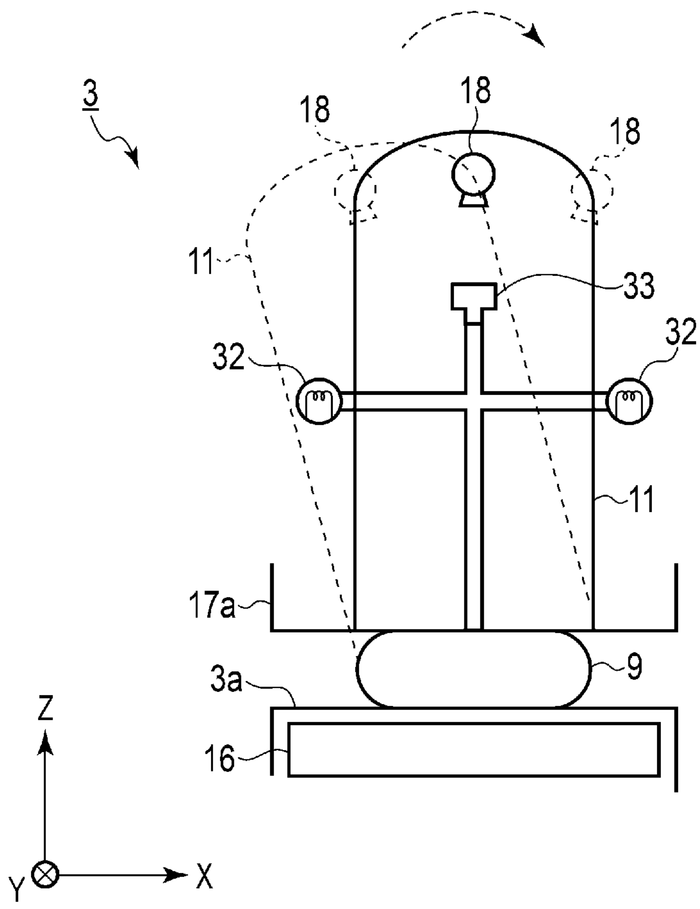
FIG. 3 is a schematic diagram for illustrating a configuration example of the X-ray imaging equipment according to the first embodiment.
Figure 4:
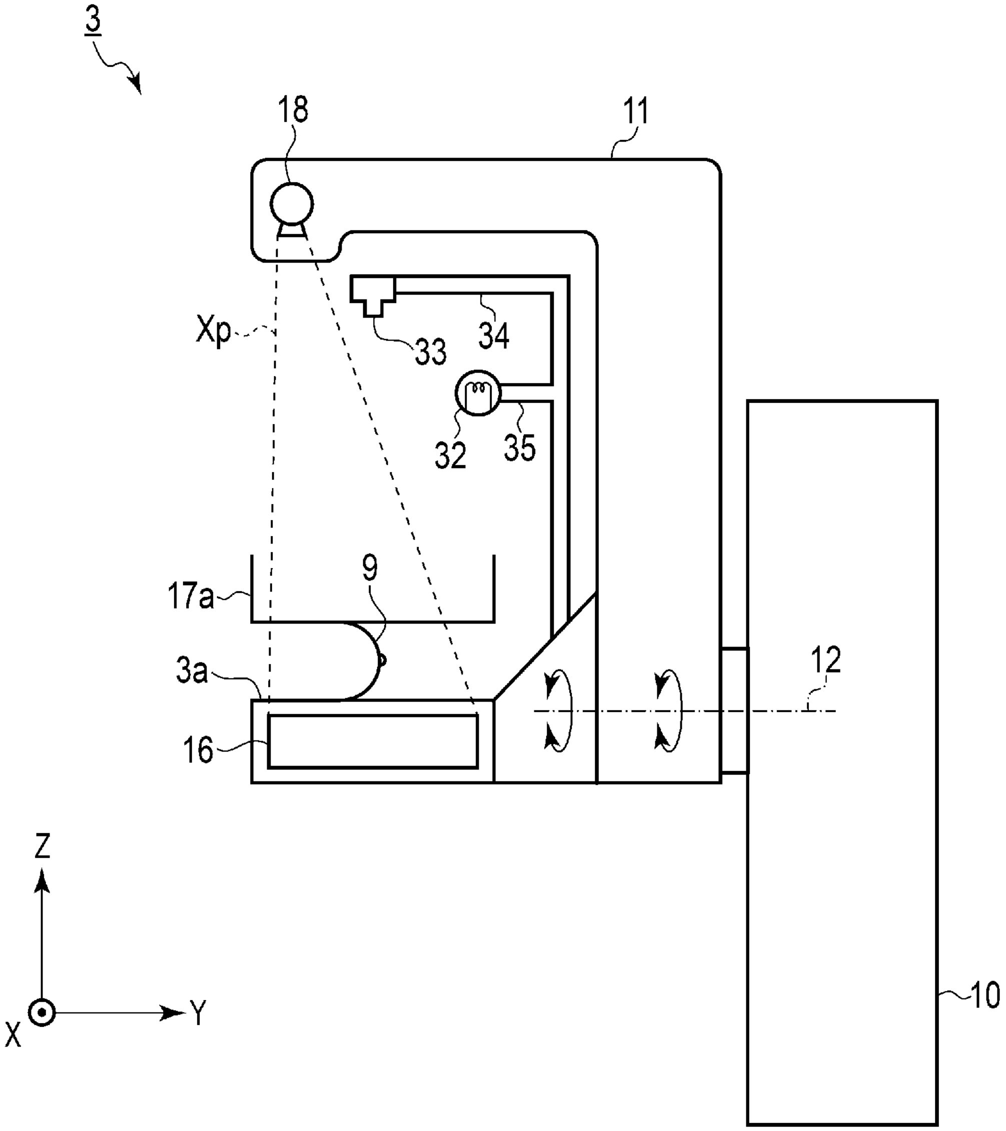
FIG. 4 is a schematic diagram for illustrating a configuration example of the X-ray imaging equipment according to the first embodiment.

FIG. 1 is a block diagram showing a configuration of an X-ray diagnostic apparatus according to a first embodiment, and FIG. 2 is a perspective view showing an example of an outer appearance of X-ray imaging equipment in the X-ray diagnostic apparatus. FIGS. 3 and 4 are schematic diagrams showing a configuration of the X-ray imaging equipment. An X-ray diagnostic apparatus 1 includes X-ray imaging equipment 3 and a computer apparatus 5.

The X-ray imaging equipment 3 includes a base unit 10, a C-arm 11, and a signal generator 31. The C-arm 11 is attached to an axial portion 12 provided at the base unit 10 so as to protrude therefrom. Thereby, the C-arm 11 is supported by the base unit 10 so as to be pivotable around a Y-axis about an axial center of the axial portion 12. Through the rotation of the C-arm 11, tomosynthesis imaging as well as normal imaging such as craniocaudal (CC) projection, mediolateral (ML) projection, and mediolateral oblique (MLO) projection can be performed. Tomosynthesis is an imaging technique of generating a plurality of tomographic images by three-dimensionally reconstructing a plurality of medical images captured from a plurality of angles by moving an X-ray tube 18. During tomosynthesis imaging, only an arm main body 14 pivots about the axial center of the axial portion 12, with a supporting base 3*a* not pivoting. Through tomosynthesis imaging of a breast, it is possible to obtain a plurality of tomographic images in which an overlap of mammary glands is reduced. It is to be noted that, in the case of normal imaging, both the arm main body 14 and the supporting base 3*a* pivot about the axial center of the axial portion 12. The signal generator 31 is capable of performing active thermography by generating a periodic signal and supplying it to a source of heat. The active thermography is a technique of evaluating the state of the surface and the interior of a measurement target utilizing, for example, a temperature change of the measurement target caused by periodically heating the measurement target from the source of heat. Such a technique is an image processing method utilizing the correlation between the cycle of heating and cooling (non-heating) applied to the measurement target and the depth of the measurement target that can be analyzed, as disclosed in Jpn. Pat. Appln. KOKAI Publication No. 2017-26422. The measurement target heated by the source of heat is, for example, cooled during the non-heating. After the end of the heating, it takes a shorter time for an infrared camera to receive infrared rays from a position (shallow position) closer to the surface of the measurement target, and it takes a longer time to receive infrared rays from a position (deep position) farther from the surface of the measurement target. Accordingly, by imaging, with an infrared camera at a predetermined frame rate, a measurement target that shows a periodic temperature change, thermographic image data corresponding to, for example, hundreds to thousands of thermographic images are generated. Also, it is possible to generate three-dimensional thermographic image data based on thermographic image data showing a state at each depth. Such three-dimensional thermographic image data is based on data of hundreds to thousands of thermographic images, and thus has a high resolution in the depth direction. In the present embodiment, it is assumed that the measurement target is a subject, and that the source of heat is a pair of flash lamps 32. That is, in the present embodiment, the subject 9 irradiated with infrared rays by the flash lamps 32 is imaged with an infrared camera 33, and thereby three-dimensional thermographic image data in which the states of the surface and the interior of the subject 9 are reflected is acquired.

The C-arm 11 is configured by attaching, to the arm main body 14, an X-ray generator 15, an X-ray detector 16, a compression unit 17, the flash lamps 32, the infrared camera 33, and supporters 34 and 35. The X-ray generator 15 and the X-ray detector 16 are arranged at both end portions of the arm main body 14. The compression unit 17 is arranged at an intermediate portion between the X-ray generator 15 and the X-ray detector 16. The flash lamps 32 are provided at both ends of the supporter 34 whose longitudinal direction is orthogonal to a longitudinal direction of the arm main body 14. The infrared camera 33 is provided at an upper end of the supporter 35 whose longitudinal direction is orthogonal to a longitudinal direction of the supporter 34. Also, the flash lamps 32, the infrared camera 33, and the supporters 34 and 35 are arranged outside an X-ray path Xp between the X-ray tube 18 and the X-ray detector 16.

The X-ray generator 15 includes the X-ray tube 18 and a high-voltage generator 19. In response to application of a tube voltage from the high-voltage generator 19 and supplying of a filament current, the X-ray tube 18 generates X-rays toward the compression unit for a predetermined X-ray duration time. The tube voltage to be applied and the X-ray duration time are adjusted to values suitable for imaging in response to a control signal from imaging control circuitry 24.

The X-ray tube 18 includes a cathode filament and an anode. Examples of the anode include a molybdenum (Mo) anode formed of Mo, a rhodium (Rh) anode formed of Rh, an Mo/Rh anode formed by mixing Mo and Rh, and a tungsten (W) anode formed of W. Such anodes can be switched whenever necessary in response to a control signal from the imaging control circuitry 24.

Upon receiving supply of a filament current, the cathode filament is heated and generates thermions. Through the tube voltage applied between the cathode filament and the anode, the generated thermions collide with the anode. By the thermions colliding with the anode, X-rays are generated. The thermions colliding with the anode allow a tube current to flow. The tube current is adjusted by the filament current. The X-ray dose during imaging is adjusted by adjusting a tube current-time product, which is a product of the tube current and the X-ray duration time, in response to a control signal from the imaging control circuitry 24.

In the X-ray tube 18, a radiation quality filter for changing the radiation quality of the generated X-rays is attached. Examples of the radiation quality filter include a Mo filter formed of Mo, an Rh filter formed of Rh, an aluminum (Al) filter formed of Al, and a filter formed of a combination of these materials. Such radiation quality filters can be switched whenever necessary in response to a control signal from the imaging control circuitry 24.

The compression unit 17 includes a compression plate 17*a* arranged so as to face the X-ray detector 16 provided at the supporting base 3*a* on which a breast is to be mounted, and supported by the C-arm 11 so as to be close to or distanced from the X-ray detector 16 along a Z-axis orthogonal to the Y-axis, around which the C-arm 11 pivots. In response to the control signal from the imaging control circuitry 24, the compression unit 17 operates the compression plate 17*a* to compress the breast of the subject 9 against the supporting base 3*a* in such a manner that the breast width falls in a predetermined range.

The X-ray detector 16 is supported by the C-arm 11 so as to be close to or distanced from the X-ray tube 18 along the imaging axis (Z-axis) connecting a center of a detection surface and a focus of the X-ray tube 18. The X-ray detector 16 is a digital detector such as a flat panel detector configured to detect X-rays that have passed through the breast. The digital detector includes a plurality of semiconductor detection elements of either a direct conversion type, which directly converts incident X-rays into an electric signal, or an indirect conversion type, which converts incident X-rays into light with a fluorescent substance and converts the light into an electric signal. The semiconductor detection elements are arrayed in a two-dimensional grid. The digital detector includes, in addition to the semiconductor detection elements such as photodiodes, an amplifier circuit and an A/D conversion circuit. Thereby, a signal charge generated in the semiconductor detection elements in accordance with the incident X-rays is output to the computer apparatus 5 as an output signal via the amplifier circuit and the A/D conversion circuit.

The signal generator 31 generates a periodic signal, and sends it to the flash lamps 32 under the control of the processing circuitry 26. The signal generator 31 may be implemented on the computer apparatus 5.

In response to the periodic signal that has been sent, the flash lamps 32 irradiate the subject 9 with infrared rays diagonally from above the subject. For the infrared rays, near-infrared rays, mid-infrared rays, far-infrared rays, or a combination of the neighboring rays may be used.

The infrared camera 33 continuously images the subject 9 periodically irradiated with infrared rays, and sends a plurality of items of thermographic image data obtained through the imaging to the computer apparatus 5. The image generation circuitry 25 of the computer apparatus 5 obtains three-dimensional thermographic image data from the plurality of items of thermographic image data that have been sent. The signal generator 31, the flash lamps 32, the infrared camera 33, and the image generation circuitry 25 are examples of a first imaging unit configured to image the subject 9 irradiated with infrared rays to obtain three-dimensional thermographic image data.

The computer apparatus 5, together with the X-ray imaging equipment 3, includes a memory 22, an input interface 23, imaging control circuitry 24, image generation circuitry 25, processing circuitry 26, a display 27, system control circuitry 28, and a network interface 29.

The memory 22 is configured of a read-only memory (ROM), a random-access memory (RAM), a hard disk drive (HDD), a memory main body configured to record electric information such as an image memory, and peripheral circuits associated with the memory main body such as a memory controller, a memory interface, etc. The memory 22 stores three-dimensional thermographic image data, X-ray image (medical image) data such as pre-imaging image data and main-imaging image data, programs, and trained models. Examples of the main-imaging image data include mammographic image data in the case of normal imaging and tomosynthesis image data in the case of tomosynthesis imaging. Examples of the programs include a medical image processing program for allowing a computer to realize a first acquisition function, a second acquisition function, a reconstruction function, and a display control function. The first acquisition function, the second acquisition function, the reconstruction function, and the display control function correspond to the respective functions of the processing circuitry 26. Examples of the trained models include a model that has been mechanically trained on a data set of the three-dimensional thermographic image data and the three-dimensional tomographic image data. The data set is created in advance by taking, as input data, the three-dimensional thermographic image data and giving, as output data, three-dimensional X-ray image data. The three-dimensional tomosynthesis image data is created by converting a size and a pixel value range of the three-dimensional thermographic image data into a size and a pixel value range of the tomosynthesis image data. The three-dimensional tomosynthesis image data obtained by converting the three-dimensional thermographic image data is also referred to as "tomosynthesis model image data". The trained model outputs, based on the three-dimensional thermographic image data, three-dimensional tomographic image data (tomosynthesis model image data).

The input interface 23 is realized by, for example, a trackball, a switch button, a mouse, or a keyboard with which an operator's various instructions, orders, information, selections, and/or settings are input to the computer apparatus 5, a touchpad with which an input operation is performed via a touch on its operation surface, or a touch panel display in which a display screen and a touchpad are integrally formed. The input interface 23 is coupled to, for example, the imaging control circuitry 24, the processing circuitry 26, etc., converts an input operation received from the operator into an electric signal, and outputs the electric signal to the imaging control circuitry 24 or the processing circuitry 26. In the description relating to the computer apparatus 5 to be given below, the expression "operator's operation" refers to an operation of the input interface 23 by the operator. Herein, the input interface 23 does not necessarily include a physical operational component, such as a mouse, a keyboard, etc. For example, electric signal processing circuitry that receives an electric signal corresponding to an input operation from an external input device provided separately from the apparatus and outputs it to the imaging control circuitry 24 or the processing circuitry 26 is also included in the examples of the input interface 23.

The input interface 23 outputs subject information transmitted from a radiology information system (RIS; not illustrated) to the processing circuitry 26 to be stored in the memory 22, in response to the operator's operation. The subject information contains, for example, a subject ID, an examination site, a purpose of examination, an age, a height, a weight, a body mass index (BMI), etc. Also, the input interface 23 is, for example, an operation panel for setting imaging conditions (the tube voltage, the tube current-time product, the material of the anode, the material of the radiation quality filter, the breast width, the Source-to-Image Distance, the magnification, etc.), the image processing conditions, etc., in the imaging control circuitry 24. Also, the input interface 23 includes an interface for operating the C-arm 11 to pivot around the Y-axis, allowing the C-arm 11 to be set at a given position. The imaging direction is determined in accordance with the set position of the C-arm 11. Also, the input interface 23 includes an interface for operating the signal generator 31 and the infrared camera 33. In response to an operation of the input interface 23, the signal generator 31 sends a periodic signal to the flash lamps 32, and the infrared camera 33 continuously images the subject 9 irradiated with infrared rays by the flash lamps 32.

The imaging control circuitry 24 includes a processor and a memory, not illustrated, and controls the constituent elements of the X-ray imaging equipment 3 based on imaging conditions set via the input interface 23, to cause the X-ray imaging equipment 3 to perform X-ray imaging and infrared imaging according to the settings.

The image generation circuitry 25 generates pre-imaging image data and main-imaging image data of a breast based on an output signal from the X-ray detector 16. The image generation circuitry 25 stores the generated data in the memory 22. The image generation circuitry 25 generates an X-ray image by, for example, subjecting pre-processing to the output signal from the X-ray detector 16. The "pre-processing" is, for example, a correction for unevenness in sensitivity between channels in the X-ray detector 16 and a correction for missing data. The image generation circuitry 25 subjects the generated X-ray image to image processing. For example, the image generation circuitry 25 subjects the generated X-ray image to a scatter correction process. The image generation circuitry 25 obtains a plurality of items of X-ray image data (a plurality of items of projection data) relating to a plurality of positions of the X-ray tube 18, which have been generated through tomosynthesis imaging. The image generation circuitry 25 stores, in the memory 22, the plurality of items of projection data obtained through the tomosynthesis imaging. The image generation circuitry 25 may send, to the processing circuitry 26, the plurality of items of projection data obtained through the tomosynthesis imaging. The X-ray tube 18, the X-ray detector 16, the C-arm 11, and the image generation circuitry 25 are examples of a second imaging unit configured to image the subject 9 with tomosynthesis and obtain a plurality of items of projection data.

The image generation circuitry 25 obtains a plurality of items of three-dimensional thermographic image data from a plurality of items of thermographic image data sent from the infrared camera 33. That is, the image generation circuitry 25 performs a lock-in process of generating three-dimensional thermographic image data as analysis images based on a phase or a temperature change amount that changes with time and that is expressed by a plurality of items of thermographic image data continuously sent from the infrared camera 33. The thermographic image data may be referred to as "thermal image data". The image generation circuitry 25 stores the obtained three-dimensional thermographic image data in the memory 22. The image generation circuitry 25 may send the obtained three-dimensional thermographic image data to the processing circuitry 26.

The processing circuitry 26 reads information and programs stored in the memory 22 based on an instruction input by an operator via the input interface 23, and controls the computer apparatus 5 in accordance therewith. The processing circuitry 26 is, for example, a processor configured to realize the functions for reconstructing tomosynthesis image data from a plurality of items of projection data based on three-dimensional thermographic image data in accordance with the program read from the memory 22, in addition to the existing function. Examples of the functions include a first acquisition function 261, a second acquisition function 262, a reconstruction function 263, and a display control function 264. The processing circuitry 26 is an example of a medical image processing apparatus.

The first acquisition function 261 acquires three-dimensional thermographic image data obtained by imaging the subject 9 irradiated with infrared rays. The first acquisition function 261 acquires three-dimensional thermographic image data from, for example, the memory 22. However, the first acquisition function 261 may acquire three-dimensional thermographic image data from the image generation circuitry 25. The first acquisition function 261 is an example of the first acquisition unit.

The second acquisition function 262 acquires a plurality of items of projection data obtained by imaging the subject 9 with tomosynthesis. The second acquisition function 262 acquires a plurality of items of projection data from, for example, the memory 22. However, the second acquisition function 262 may acquire a plurality of items of projection data from the image generation circuitry 25. The second acquisition function 262 is an example of the second acquisition unit.

The reconstruction function 263 performs reconstruction based on a plurality of items of projection data and three-dimensional thermographic image data. For example, the reconstruction function 263 iteratively executes reconstruction to decrease a difference between tomosynthesis image data obtained by executing reconstruction and tomosynthesis model image data corresponding to the three-dimensional thermographic image data. The reconstruction function 263 generates the tomosynthesis model image data by converting a size and a pixel value range of the three-dimensional thermographic image data into a size and a pixel value range of the tomosynthesis image data. Specifically, the reconstruction function 263 may generate tomosynthesis model image data by inputting three-dimensional thermographic image data to a trained model read from the memory 22. The reconstruction function 263 is an example of a reconstruction unit.

The display control function 264 allows medical images such as pre-imaging images, main-imaging images, three-dimensional thermographic images, and tomosynthesis images to be displayed on the display 27. The display control function 264 is an example of a display control unit.

The display 27 is configured of a display main body configured to display medical images such as a pre-imaging image and a main-imaging image, internal circuitry configured to supply a signal for display on the display main body, and peripheral circuits such as a cable and a connector for connecting the display main body and the internal circuitry. The display 27 is controlled by the processing circuitry 26, and is an example of a display unit for displaying medical images, etc.

The system control circuitry 28 includes a memory and a processor (not illustrated), and controls the constituent elements, functioning as the nerve center of the X-ray diagnostic apparatus 1.

The network interface 29 is circuitry for connecting the computer apparatus 5 to a network Nw to allow communication with an external device (not illustrated). Examples of the network interface 29 that can be used include a network interface card (NIC).

The computer apparatus 5 and the X-ray imaging equipment 3 may be integrally formed.

Figure 5:
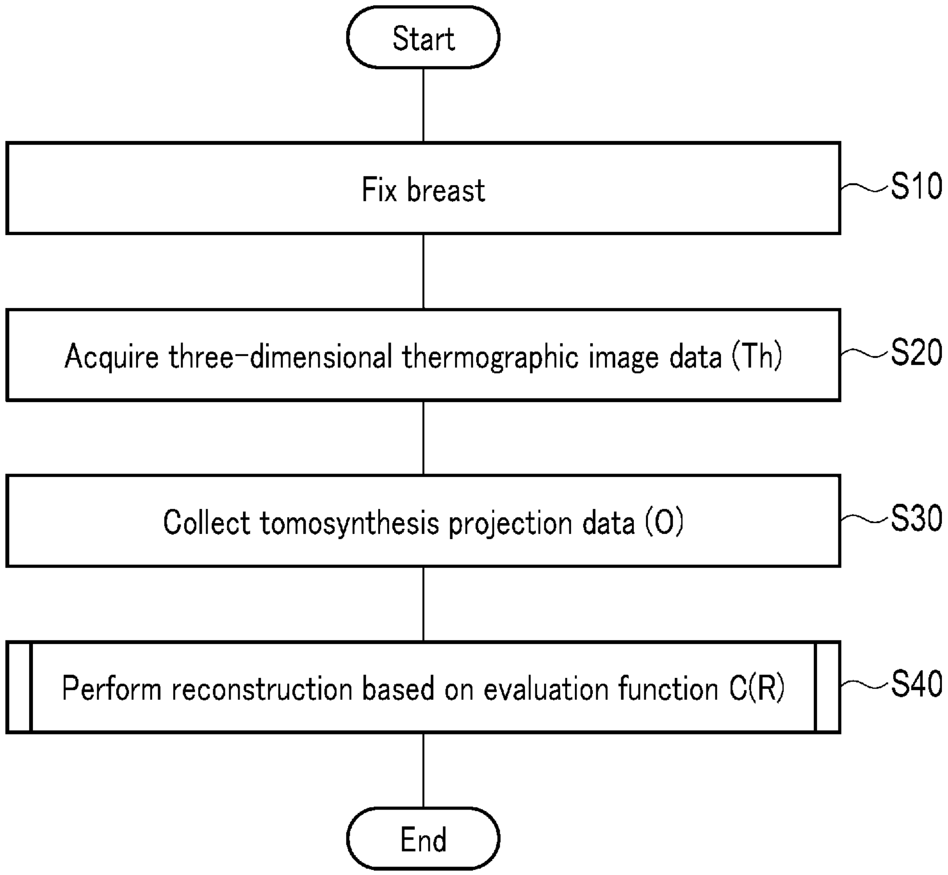
FIG. 5 is a flowchart for illustrating an operation according to the first embodiment.
Figure 7:
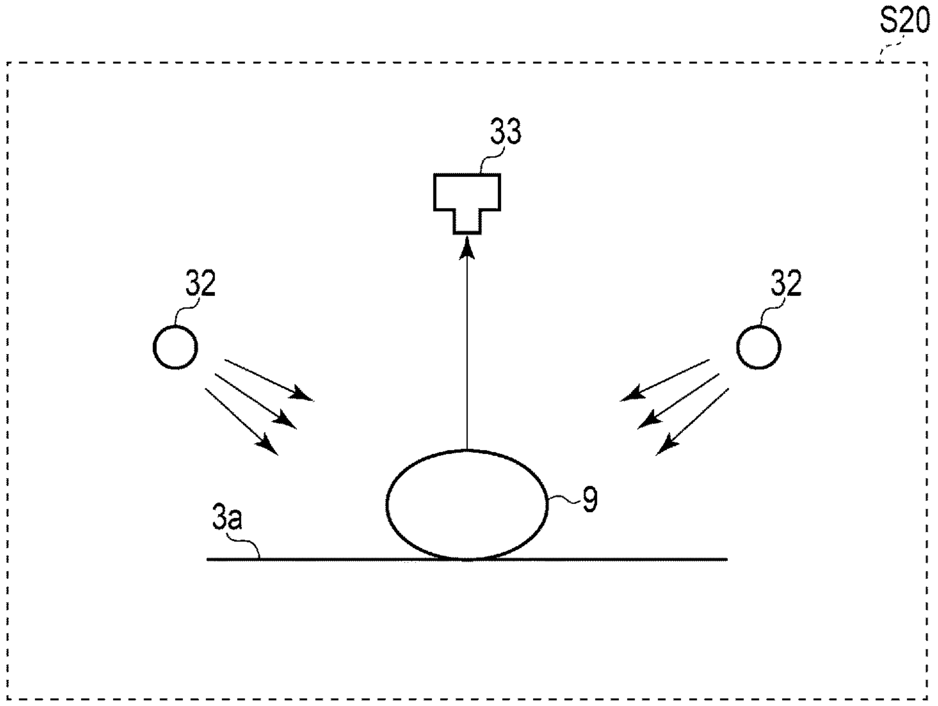
FIG. 7 is a schematic diagram for illustrating an operation at step S20 in FIG. 5.
Figure 8:
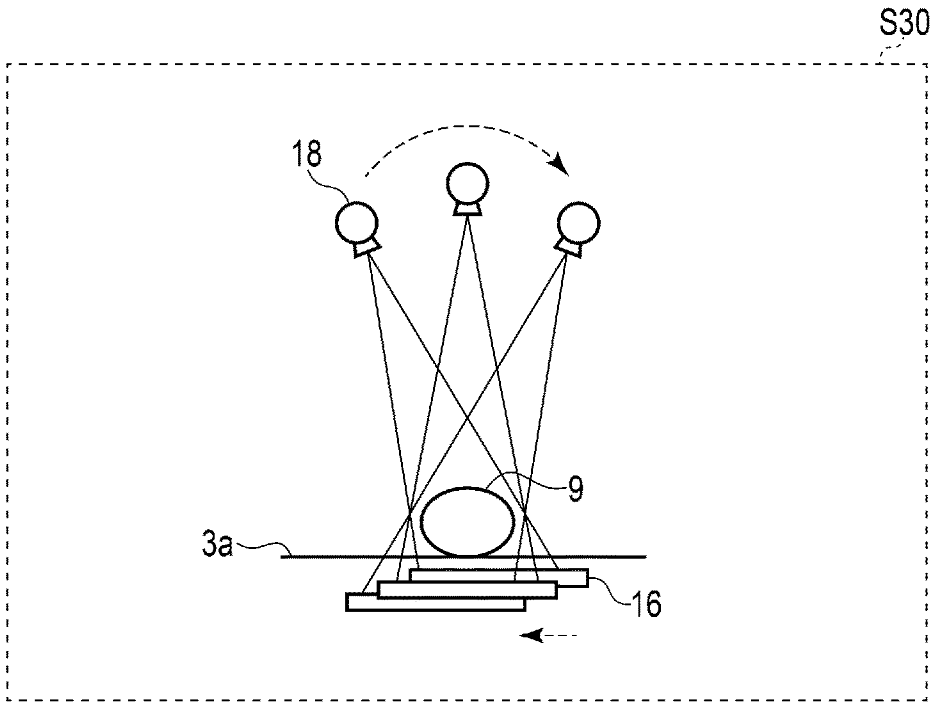
FIG. 8 is a schematic diagram for illustrating an operation at step S30 in FIG. 5.

Next, an operation of the X-ray diagnostic apparatus with the above-described configuration will be described using the flowcharts shown in FIGS. 5 and 6 and the schematic diagrams shown in FIGS. 7 to 8.

It is assumed that, in the X-ray diagnostic apparatus 1, subject information transmitted from an RIS, for example, is stored in the memory 22. The subject information contains, for example, a subject ID, an examination site, a purpose of examination, an age, a height, a weight, a body mass index (BMI), etc. It is also assumed that a mammography examination of a breast of the subject 9 is to be performed based on the subject information.

At step S10, in the X-ray diagnostic apparatus 1, a breast of the subject 9 is mounted on the supporting base 3*a*, compressed by the compression plate 17*a*, and fixed onto the supporting base 3*a*, in response to the operator's operation. At this time, in the X-ray diagnostic apparatus 1, a breast width, a resistance, etc. in a compressed state are acquired.

After step S10, the X-ray diagnostic apparatus 1 performs, at step S20, imaging of the fixed breast with active thermography, in response to the operator's operation. That is, in the X-ray diagnostic apparatus 1, the signal generator 31 generates a periodic signal and sends it to the flash lamps 32. In response to the periodic signal that has been sent, the flash lamps 32 irradiate the breast of the subject 9 with infrared rays diagonally from above the breast, as shown in FIG. 7. The infrared camera 33 continuously images the breast of the subject 9 periodically irradiated with infrared rays, and sends a plurality of items of thermographic image data obtained through the imaging to the computer apparatus 5. The image generation circuitry 25 of the computer apparatus 5 performs a lock-in process based on the plurality of items of thermographic image data that have been sent, and obtains three-dimensional thermographic image data. Thereafter, the image generation circuitry 25 stores the obtained three-dimensional thermographic image data in the memory 22. Thereby, the processing circuitry 26 acquires the three-dimensional thermographic image data in the memory 22. Herein, the acquired three-dimensional thermographic image data will be denoted by a "vector Th". The vector Th is a column vector containing, as elements, pixel values of the three-dimensional thermographic image data.

After step S20, the X-ray diagnostic apparatus 1 images, at step S30, the breast of the subject 9 with tomosynthesis, triggered by completion of acquisition of the vector Th. That is, the X-ray diagnostic apparatus 1 issues a signal from the imaging control circuitry 24 to a rotation control device (not illustrated) in the X-ray imaging equipment 3, triggered by completion of acquisition of the vector Th, and causes the C-arm 11 to pivot to a preset angle. If the angle of the C-arm 11 has reached a specified angle, as shown in FIG. 8, the imaging control circuitry 24 issues a command to the rotation control device, and causes the C-arm 11 to pivot in the direction of the arrow with constant velocity. After the pivoting has started, the imaging control circuitry 24 generates a signal at a frame rate (e.g., 2 fps, 4 fps, etc.) suitable for collection of projection data in tomosynthesis imaging. The generated signal is received by the high-voltage generator 19 and the X-ray detector 16. At the high-voltage generator 19, X-rays are generated from the X-ray tube 18. A breast of the subject 9 is irradiated with the generated X-rays via the compression plate 17*a*. Thereby, in the X-ray diagnostic apparatus 1, as shown in FIG. 8, X-ray irradiation is performed from the X-ray tube 18 at a plurality of irradiation angles. The X-rays that have passed through the breast of the subject 9 are detected by the X-ray detector 16, and an output signal corresponding to the detected X-ray dose is output to the computer apparatus 5. The image generation circuitry 25 of the computer apparatus 5 receives, from the X-ray detector 16, an output signal corresponding to the X-ray dose detected by the X-ray detector 16, and subjects the output signal to image processing, thereby obtaining a plurality of items of projection data representing the breast of the subject 9. Thereafter, the image generation circuitry 25 stores the obtained plurality of items of projection data in the memory 22. If a predetermined irradiation angle has been reached, or if the number of X-ray irradiations has reached a predetermined number, the imaging control circuitry 24 issues a command to the rotation control device, stops rotation of the C-arm 11, generation of the X-rays, and detection of the X-rays at the X-ray detector 16, thereby ending the tomosynthesis imaging. Thereby, the processing circuitry 26 acquires a plurality of items of projection data in the memory 22. Here, the plurality of items of projection data (plurality of items of two-dimensional X-ray image data) acquired through tomosynthesis will be denoted by a "vector O". The vector O is a column vector containing, as elements, pixel values of the plurality of items of projection data.

After step S30, the processing circuitry 26 of the X-ray diagnostic apparatus 1 executes, at step S40, reconstruction based on the vector O describing the plurality of items of projection data and the vector Th describing the three-dimensional thermographic image data. Specifically, the processing circuitry 26 performs iterative reconstruction based on an evaluation function C(R) based on Formula (1) below.

$$C(R) = \frac{1}{2}(P*R-O)^2 + \alpha\frac{1}{2}(R-X*Th)^2 \tag{1}$$

Here, P is a matrix for performing a forward projection. R is a vector of tomosynthesis image data. More specifically, R is a column vector containing, as elements, pixel values of the tomosynthesis image data. Here, α is a scalar parameter indicating a rate at which image information of the vector Th is introduced, and is a real number equal to or greater than 0 and equal to or smaller than 1. Since α=0 is set in the case where image information of the vector Th is not introduced, α is, in normal cases, a real number greater than 0 and equal to or smaller than 1. The parameter α can be obtained empirically, for example. X is a determinant that converts three-dimensional thermographic image data into tomographic model image data (three-dimensional X-ray image data). The determinant X is for generating tomosynthesis model image data by, for example, converting a size and a pixel value range of the three-dimensional thermographic image data into a size and a pixel value range of the tomosynthesis image data. In the evaluation function C(R), the first term on the right hand, "(½)*(P*R–O)^2" (where "^" is a notation representing exponentiation), is a term relating to a squared error between a plurality of items of projection data (P*R) obtained by a forward projection of the tomosynthesis image data and the plurality of items of projection data (O) acquired through tomosynthesis. The second term on the right hand, "(R–X*Th)^2", is a term relating to a multiplication by a parameter (α times) of a squared error between the tomosynthesis image data (R) obtained through the execution of the reconstruction and tomosynthesis model image data (X*Th) corresponding to the three-dimensional thermographic image data.

Figure 6:
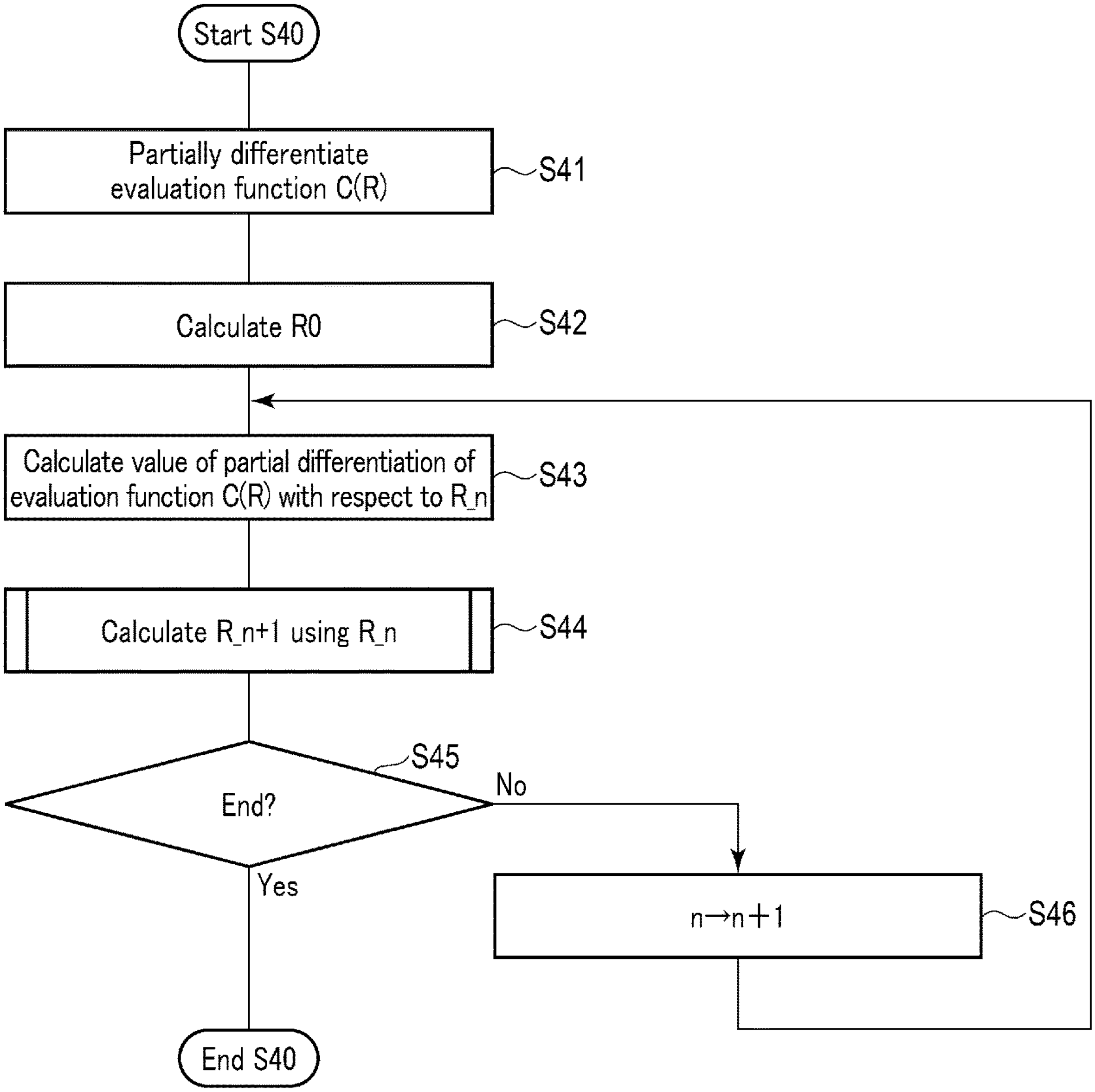
FIG. 6 is a flowchart for illustrating an operation at step S40 in FIG. 5.

Step S40 is executed by steps S41 to S46 as shown in FIG. 6.

At step S41, the processing circuitry 26 calculates partial differentiation of the evaluation function C(R), as shown in Formula (2) below. The processing circuitry 26 may read Formula (2) from the memory 22. Formula (2) indicates a formula in which the evaluation function C(R) is partially differentiated with respect to a vector R.

$$\frac{\partial}{\partial R}C(R) = P^{-1}(P*R-O) + \alpha(R-X*Th) \tag{2}$$

More specifically, Formula (2) represents a sum of first tomosynthesis error image data (P^–1 (P*R–O)) obtained by a back projection of an error between the plurality of items of projection data (P*R) obtained by the forward projection and the plurality of items of projection data (O) acquired through tomosynthesis, and second tomosynthesis error image data (α (R–X*Th)) obtained by multiplying, by a parameter α, an error between the tomosynthesis image data (R) and the tomosynthesis model image data (X*Th). Similarly to the above-described configuration, α indicates a rate at which image information of the vector Th (errors relating to three-dimensional thermographic image data) is introduced, as described above.

After step S41, the processing circuitry 26 calculates, at step S42, vector R_0 as an initial value (if n=0) of n-th tomosynthesis image data. All the elements of the vector R_0 may be 0 values; alternatively, pixel values obtained by filtered back projection may be contained as the elements.

After step S42 or S46, the processing circuitry 26 calculates, at step S43, a value of partial differentiation of the evaluation function C(R) with respect to the vector R_n in accordance with Formula (2). If it is the first time that S43 is executed after step S42 (if n=0), the vector R_n is the vector R_0. Here, n is the number of iterations of steps S43 to S46, and since an iteration has not been performed during the first time, n=0 is satisfied. That is, n is a non-negative integer that is zero or a natural number.

After step S43, the processing circuitry 26 calculates, at step S44, vector R_n+1 of the (n+1)-th tomosynthesis image data using the vector R_n, as shown by Formula (3) below.

If n=0, the processing circuitry 26 calculates, using vector R_0, vector R_1.

$$R_{n+1} = R_n - \beta \frac{\partial}{\partial R} C(R) \quad (3)$$

Here, β is a parameter determining the speed at which an image is updated, and is a real number greater than 0 and equal to or smaller than 1. That is, the processing circuitry 26 calculates a vector R_n+1 by subtracting, from the vector R_n, a value obtained by multiplying the value obtained by the partial differentiation by the parameter β.

After step S44, the processing circuitry 26 determines, at step S45, whether or not an update loop including step S43 of obtaining a value obtained by partially differentiating an evaluation function and step S44 of updating tomosynthesis image data is to be ended. Specifically, the processing circuitry 26 determines that the update loop is to be ended if an exit condition is satisfied. The exit condition is satisfied if, for example, a difference between pre-update tomosynthesis image data and post-update tomosynthesis image data has fallen below a threshold value, or if the number of iterations of the update loop has reached a maximum number. The difference corresponds to a difference between the vectors R_n and R_n+1. If it is determined at step S45 that the update loop is not to be ended, the procedure shifts to step S46.

After step S45, the processing circuitry 26 updates, at step S46, the number of iterations "n" to "n+1", and shifts to step S43. Thereafter, the update loop from steps S43 to S46 is iteratively executed until the exit condition used at step S45 is satisfied. In accordance therewith, the processing circuitry 26 iteratively executes reconstruction to reduce errors between the tomosynthesis image data (R) obtained through execution of reconstruction and tomosynthesis model image data (X*Th) corresponding to the three-dimensional thermographic image data (Th).

On the other hand, if it is determined at step S45 that the update loop is to be ended, the processing at step S40, configured of steps S41 to S46, is ended.

After step S40, the processing circuitry 26 causes the display 27 to display tomosynthesis images based on tomosynthesis image data. The tomosynthesis images are obtained using three-dimensional thermographic images as a model, and are required to have a higher resolution in the depth direction. That is, it is possible to obtain tomosynthesis images as if they were collected from a great depth.

According to the first embodiment described above, the processing circuitry 26 acquires three-dimensional thermographic image data obtained by imaging the subject 9 irradiated with infrared rays. The processing circuitry 26 acquires a plurality of items of projection data obtained by imaging the subject 9 with tomosynthesis. The processing circuitry 26 executes reconstruction based on a plurality of items of projection data and three-dimensional thermographic image data. It is thus possible to increase the resolution in the depth direction without widening the range of irradiation angles in tomosynthesis imaging. Also, since the range of irradiation angles (swing angle) in tomosynthesis imaging can be decreased, it is possible to achieve improvement in throughput and reduction in exposure dose.

Moreover, according to the first embodiment, the processing circuitry 26 iteratively executes reconstruction to reduce errors between the tomosynthesis image data obtained through execution of reconstruction and tomosynthesis model image data corresponding to the three-dimensional thermographic image data. In this case, it is possible to perform successive-approximation reconstruction, which reduces errors according to the number of iterations, in addition to the above-described effects.

Furthermore, according to the first embodiment, the processing circuitry 26 generates tomosynthesis model image data by converting a size and a pixel value range of the three-dimensional thermographic image data into a size and a pixel value range of the tomosynthesis image data. In this case, it is possible to easily generate tomosynthesis model image data (three-dimensional X-ray image data) corresponding to the three-dimensional thermographic image data, in addition to the above-described effects.

Moreover, according to the first embodiment, the processing circuitry 26 iteratively executes reconstruction based on an evaluation function relating to a squared error between a plurality of items of projection data obtained by a forward projection of the tomosynthesis image data and the plurality of items of projection data acquired through tomosynthesis, and a squared error between tomosynthesis image data obtained through execution of reconstruction and tomosynthesis model image data corresponding to the three-dimensional thermographic image data. In this case, it is possible to iteratively execute the reconstruction to reduce errors relating to tomosynthesis images and errors relating to three-dimensional thermographic images, in addition to the above-described effects.

Furthermore, according to the first embodiment, the processing circuitry 26 partially differentiates an evaluation function with respect to tomosynthesis image data, and updates the tomosynthesis image data based on a result of the partial differentiation. In this case, it is possible to easily update tomosynthesis image data, in addition to the above-described effects.

Moreover, according to the first embodiment, the processing circuitry 26 iterates an update loop including partial differentiation of the evaluation function and updating of tomosynthesis image data until the exit condition is satisfied. In this case, it is possible to perform successive-approximation reconstruction, which reduces errors according to the exit condition, in addition to the above-described effects.

Furthermore, according to the first embodiment, the exit condition is satisfied if, for example, a difference between pre-update tomosynthesis image data and post-update tomosynthesis image data has fallen below a threshold value, or if the number of iterations of the update loop has reached a maximum number. In this case, it is possible to perform successive-approximation reconstruction according to the maximum number of iterations or the threshold value of the difference, in addition to the above-described effects.

Moreover, according to the first embodiment, a result obtained by partial differentiation is a sum of first tomosynthesis error image data obtained by a back projection of an error between a plurality of items of projection data obtained by a forward projection and a plurality of items of projection data acquired through tomosynthesis and second tomosynthesis error image data obtained by multiplying, by a parameter, an error between tomosynthesis image data and tomosynthesis model image data. Also, a parameter α used in the multiplication by the parameter indicates a rate at which errors relating to three-dimensional thermographic image data are introduced. In this case, it is possible to update the tomosynthesis image data based on a result of partial differentiation including errors relating to the three-dimensional thermographic image data at a ratio corresponding to the parameter α, in addition to the above-described effects.

<Modifications>

In the first embodiment, a mammographic apparatus is used as the X-ray diagnostic apparatus; however, the configuration is not limited thereto. For example, a given X-ray apparatus configured to perform tomosynthesis imaging, such as an X-ray fluoroscopic apparatus and a general X-ray imaging apparatus, can be used as the X-ray diagnostic apparatus.

In the first embodiment, a breast of the subject is imaged; however, the configuration is not limited thereto. For example, a site with a small thickness (thin site), such as a limb, may be imaged by the X-ray fluoroscopic apparatus. Since the temperature of the subject needs to be changed by infrared irradiation up to the deep portion to acquire three-dimensional thermographic image data, it is preferable that a site with a relatively small thickness, such as a breast and a limb, be imaged.

In the first embodiment, two flash lamps 32 are used to irradiate a subject with infrared rays; however, the configuration is not limited thereto. For example, one or three or more flash lamps 32 may be used to perform infrared irradiation. With such modification, it is possible to obtain similar effects as can be obtained by the first embodiment.

In the first embodiment, the flash lamps 32 are provided in an exposed manner, as shown in FIGS. 2 to 4; however, the configuration is not limited thereto. For example, the flash lamps 32 may be sheathed with a cover that includes an opening in a direction of a site to be imaged (e.g., a breast). In this case, it is possible to protect a site of the subject other than the site to be imaged from infrared irradiation, in addition to the above-described effects.

In the first embodiment, the acquired three-dimensional thermographic image data is used as it is; however, the configuration is not limited thereto. For example, three-dimensional thermographic image data for calibration (hereinafter, "calibration image data") may be obtained in advance by imaging a phantom irradiated with infrared rays, calibrating three-dimensional thermographic image data of the subject with the calibration image data, and performing reconstruction using the calibrated three-dimensional thermographic image data. In this case, it is possible to execute reconstruction with a higher precision, in addition to the effects of the first embodiment.

In the first embodiment, tomosynthesis projection data is collected after acquisition of three-dimensional thermographic image data; however, the configuration is not limited thereto. For example, three-dimensional thermographic image data may be acquired after collection of tomosynthesis projection data. With such modification, it is possible to obtain similar effects as can be obtained by the first embodiment.

Modifications of the first embodiment have been described above. These modifications can be similarly applied to the embodiments to be described below.

Second Embodiment

In a second embodiment, a subject 9 into which a medication that generates heat through infrared irradiation has been administered is irradiated with infrared rays, unlike the first embodiment in which a normal subject 9 is irradiated with infrared rays. That is, the second embodiment is designed to emphasize a tumor in three-dimensional thermographic image data by administering a medication that generates heat through infrared irradiation.

This type of medication is disclosed in, for example, the following URL:

"Detection and treatment of cancer in mice using nanoparticles and near-infrared laser light through development of gamma-ray crosslinked gelatin-liquid metal nanoparticles", National Institutes for Quantum Science and Technology, press release updated on Dec. 21, 2021 <URL: https://www.qst.go.jp/site/press/20211221.html>

According to the disclosure, gamma-ray crosslinked gelatin-liquid metal nanoparticles (hereinafter simply referred to as a "medication") accumulate in a tumor by the enhanced permeation and retention (EPR) effect, and a cancer-affected area can be visualized by a biologically permeable near-infrared laser, and heat can be generated by photothermal conversion. The EPR effect is an effect that allows nanoparticles controlled to have a size equal to or smaller than 100 nm to not be leaked to normal tissues but to reach cancer tissues and accumulate in the affected area only from the tumor blood vessels.

In accordance therewith, the first acquisition function 261 of the processing circuitry 26 acquires three-dimensional thermographic image data relating to the subject 9 into which the medication that generates heat through infrared irradiation has been administered, in addition to the above-described function.

Also, it is preferable that the parameter α have a greater value in the case where a medication that generates heat through infrared irradiation is administered into the subject 9 than in the case where such a medication is not administered. In addition to the above-described function, the reconstruction function 263 of the processing circuitry 26 includes a function of setting the parameter α to have a greater value in the case where a medication that generates heat through infrared irradiation is administered into the subject 9 than in the case where such a medication is not administered. However, the processing circuitry 26 is not limited to the setting function, and may include a function of causing the display 27 to display a message prompting setting of a greater value as the parameter α.

The other configurations are similar to those of the first embodiment.

Figure 9:
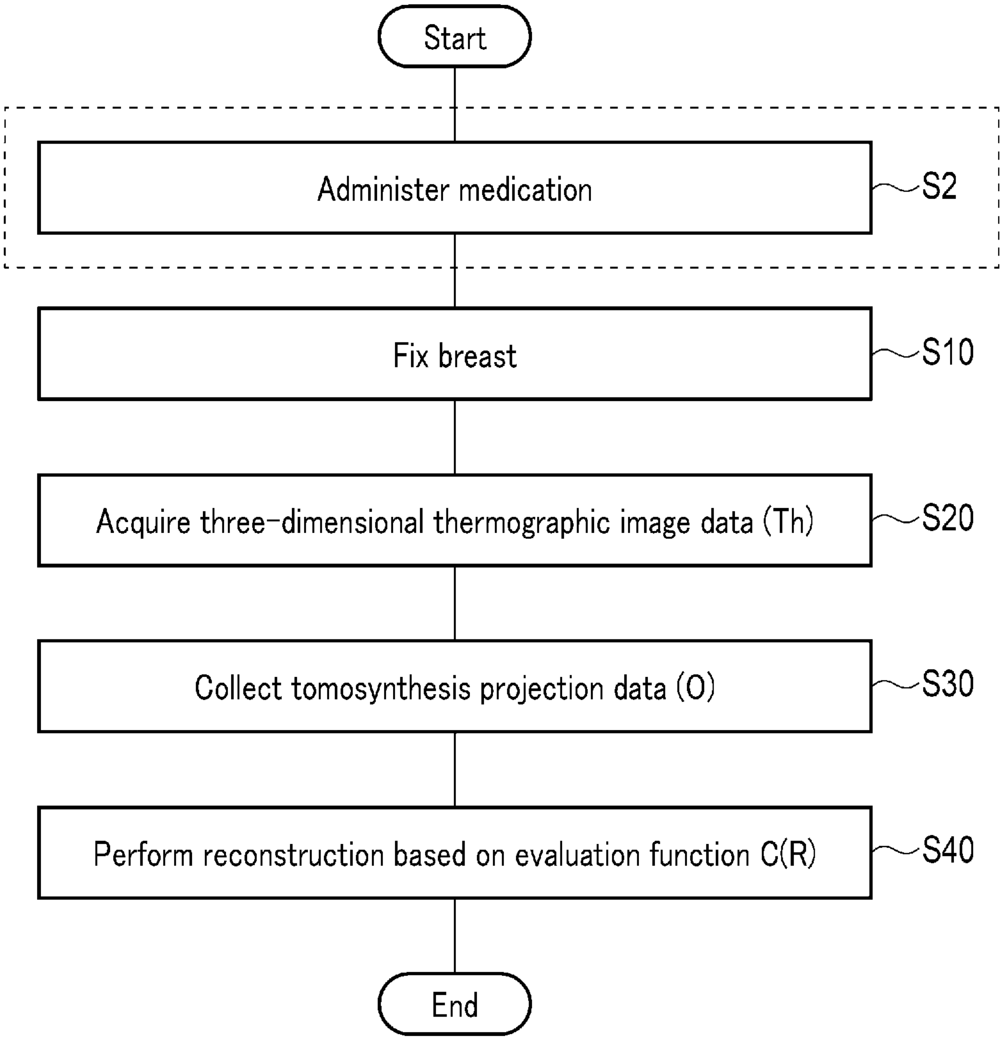
FIG. 9 is a flowchart for illustrating an operation according to a second embodiment.

Next, an operation of the X-ray diagnostic apparatus with the above-described configuration will be described with reference to the flowchart in FIG. 9.

It is assumed that, in the X-ray diagnostic apparatus 1, subject information transmitted from an RIS, for example, is stored in the memory 22, similarly to the above-described configuration. It is also assumed that a mammography examination of a breast of the subject 9 is to be performed based on the subject information.

In this case, at step S2, the medication that generates heat through infrared irradiation is administered into the subject 9. Also, the processing circuitry 26 sets the parameter α to have a greater value in the case where a medication is administered than in the case where such a medication is not used.

After step S2, similarly to the above-described configuration, step S10 is executed, and a breast of the subject 9 is fixed onto the supporting base 3*a*.

After step S10, step S20 is executed, similarly to the above-described configuration. However, the breast of the subject 9 irradiated with infrared rays gets hot at a region at which the medication is condensed. Accordingly, in the processing circuitry 26, three-dimensional thermographic image data (Th) in which a portion in which the medication accumulates is enhanced is acquired.

After step S20, step S30, in which tomosynthesis imaging is performed, is executed, similarly to the above-described configuration.

After step S30, step S40 is executed, similarly to the above-described configuration. Of step S40, at step S43 at which the value of partial differentiation is calculated, the rate at which information of three-dimensional thermographic image data (Th) is introduced increases in accordance with the value of the parameter α. As a result, accumulation of the medication is reflected in the reconstructed tomosynthesis image data (R).

As described above, according to the second embodiment, the parameter α has a greater value in the case where a medication that generates heat through infrared irradiation is administered than in the case where such a medication is not administered. It is thus possible to reconstruct tomosynthesis images with a further emphasis on a tumor, in addition to the effects of the first embodiment.

Moreover, according to the second embodiment, the processing circuitry 26 acquires three-dimensional thermographic image data relating to a subject into which a medication that generates heat through infrared irradiation has been administered. It is thus possible to reconstruct tomosynthesis images having a high diagnostic ability, in addition to the effects of the first embodiment.

<Modifications>

In the second embodiment, gamma-ray crosslinked gelatin-liquid metal nanoparticles are taken as an example of the medication; however, the configuration is not limited thereto. For example, a given medication that similarly accumulates in a tumor and generates heat through infrared radiation can be used. The modifications of the second embodiment can be similarly applied to the embodiments to be described below.

Third Embodiment

In the third embodiment, imaging with infrared irradiation and tomosynthesis imaging are executed in parallel, unlike the first embodiment in which imaging with infrared irradiation and tomosynthesis imaging are executed in sequence. That is, the third embodiment is designed to reduce the examination time by executing the two types of imaging in parallel.

Here, imaging through infrared irradiation is executed by a first imaging unit including a signal generator 31, flash lamps 32, an infrared camera 33, and image generation circuitry 25. The first imaging unit images the subject 9, and obtains three-dimensional thermographic image data acquired by the first acquisition function 261 of the processing circuitry 26.

Similarly, the tomosynthesis imaging is executed by a second imaging unit including the X-ray tube 18, the X-ray detector 16, the C-arm 11, and the image generation circuitry 25. The second imaging unit images the subject 9 with tomosynthesis, and obtains a plurality of items of projection data to be acquired by the second acquisition function 262 of the processing circuitry 26.

The imaging control circuitry 24 causes imaging with the first imaging unit and tomosynthesis imaging with the second imaging unit to be executed in parallel. The imaging control circuitry 24 starts collecting a plurality of items of projection data in such a manner that a timing of acquiring three-dimensional thermographic image data and a timing of starting reconstruction become approximately the same. For example, since the time of imaging with the first imaging unit and the time of imaging with the second imaging unit are known, the imaging control circuitry 24 controls the timings of starting imaging with the first imaging unit and the second imaging unit in such a manner that the timings of ending the imaging with the first imaging unit and the second imaging unit become approximately identical. The imaging control circuitry 24 is an example of a control unit.

The other configurations are similar to those of the first embodiment.

Figure 10:
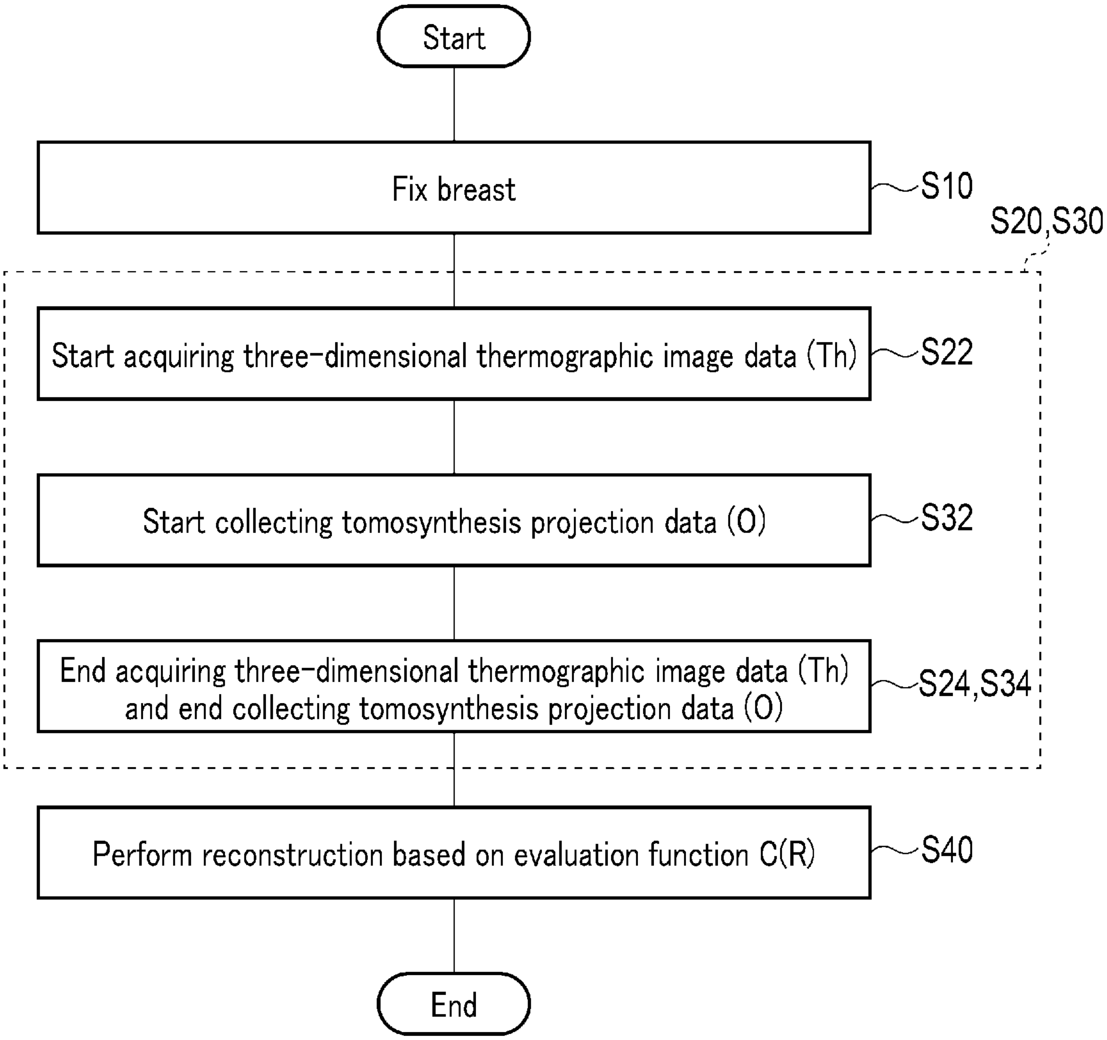
FIG. 10 is a flowchart for illustrating an operation according to a third embodiment.

Next, an operation of the X-ray diagnostic apparatus with the above-described configuration will be described with reference to the flowchart in FIG. 10.

First, the X-ray diagnostic apparatus 1 executes step S10, and a breast of the subject 9 is fixed onto the supporting base 3*a*, similarly to the above-described configuration.

After step S10, the above-described steps S20 and S30 are executed in parallel.

At step S22, the imaging control circuitry 24 controls the first imaging unit to start imaging with active thermography. Thereby, the first imaging unit including the signal generator 31, the flash lamps 32, the infrared camera 33, and the image generation circuitry 25 starts acquiring three-dimensional thermographic image data.

After step S22, the imaging control circuitry 24 controls, at step S32, the second imaging unit to start tomosynthesis imaging. Thereby, the second imaging unit including the X-ray tube 18, the X-ray detector 16, the C-arm 11, and the image generation circuitry 25 starts collecting a plurality of items of projection data.

After step S32, the processing circuitry 26 ends acquiring the three-dimensional thermographic image data, and ends collecting the projection data at steps S24 and S34. Thereby, steps S20 and S30 end.

After the end of steps S20 and S30, the processing at step S40 and thereafter is executed, similarly to the above-described configuration.

According to the third embodiment described above, the first imaging unit images the subject 9, and obtains three-dimensional thermographic image data to be acquired by the first acquisition unit. The second imaging unit images the subject 9 with tomosynthesis, and obtains a plurality of items of projection data to be acquired by the processing circuitry 26. The imaging control circuitry 24 causes imaging with the first imaging unit and tomosynthesis imaging with the second imaging unit to be executed in parallel. With the above-described configuration in which imaging with the first imaging unit and imaging with the second imaging unit are executed in parallel, it is possible to reduce the examination time, in addition to the effects of the first embodiment.

<Modifications>

The third embodiment is applied to the first embodiment in which a normal subject 9 is irradiated with infrared rays; however, the configuration is not limited thereto. That is, the third embodiment may be applied to the second embodiment in which a subject 9 into which a medication that generates heat through infrared irradiation has been administered is irradiated with infrared rays. In this case, the effects of both of the second and third embodiments can be obtained.

Fourth Embodiment

In the fourth embodiment, unlike the first embodiment in which only three-dimensional thermographic image data is acquired through infrared irradiation from above, three-dimensional thermographic image data is further acquired through infrared irradiation from below. More specifically, the fourth embodiment takes into consideration the case where the breast has a large thickness, which tends to cause a decrease in the resolution of the three-dimensional thermographic image data on the lower side. That is, the fourth embodiment is designed to improve the resolution of the lower side of the three-dimensional thermographic image data by acquiring and merging a plurality of items of three-dimensional thermographic image data captured from diametrically opposite directions.

Figure 11:
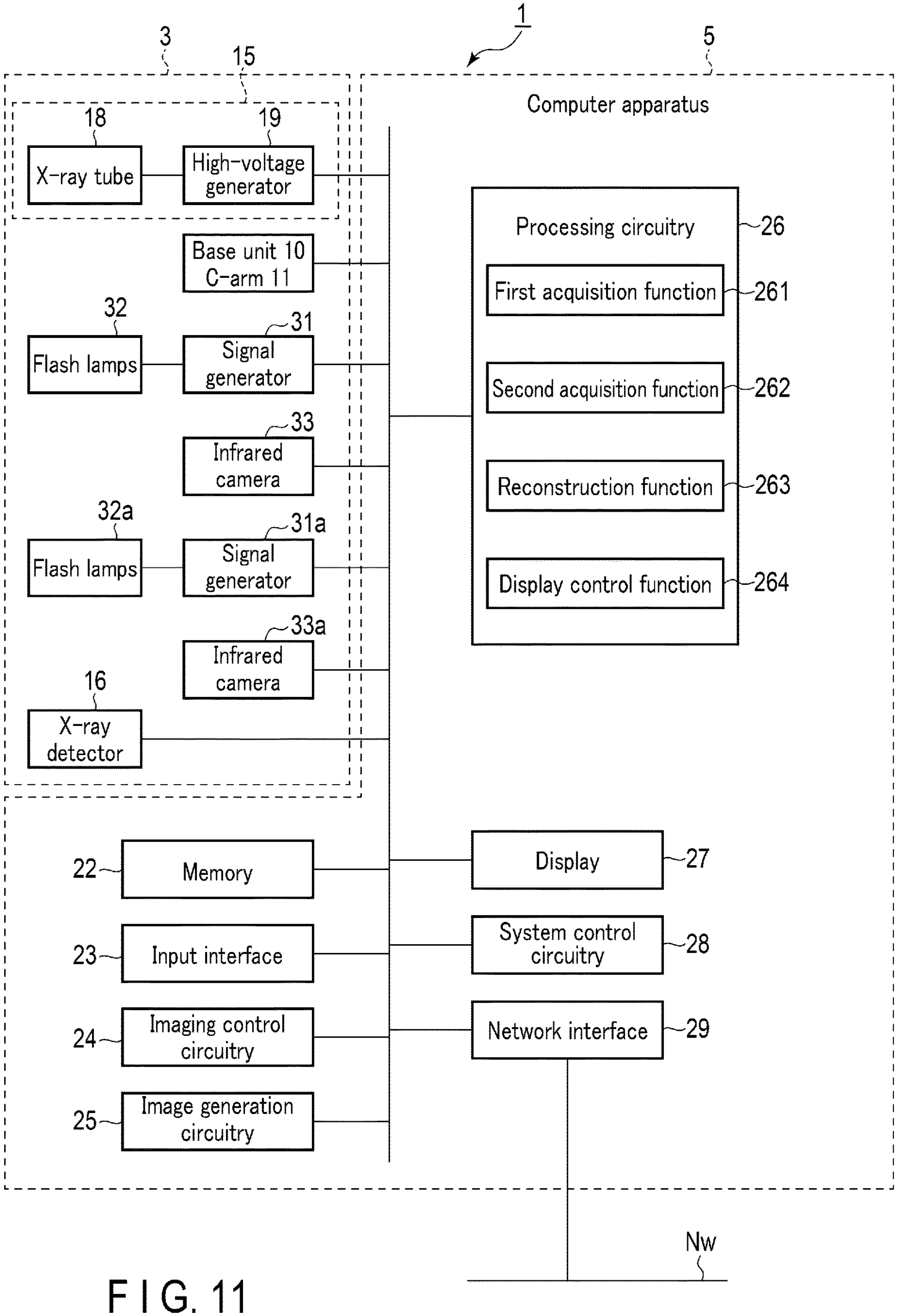
FIG. 11 is a block diagram showing a configuration example of an X-ray diagnostic apparatus according to a fourth embodiment.
Figure 12:
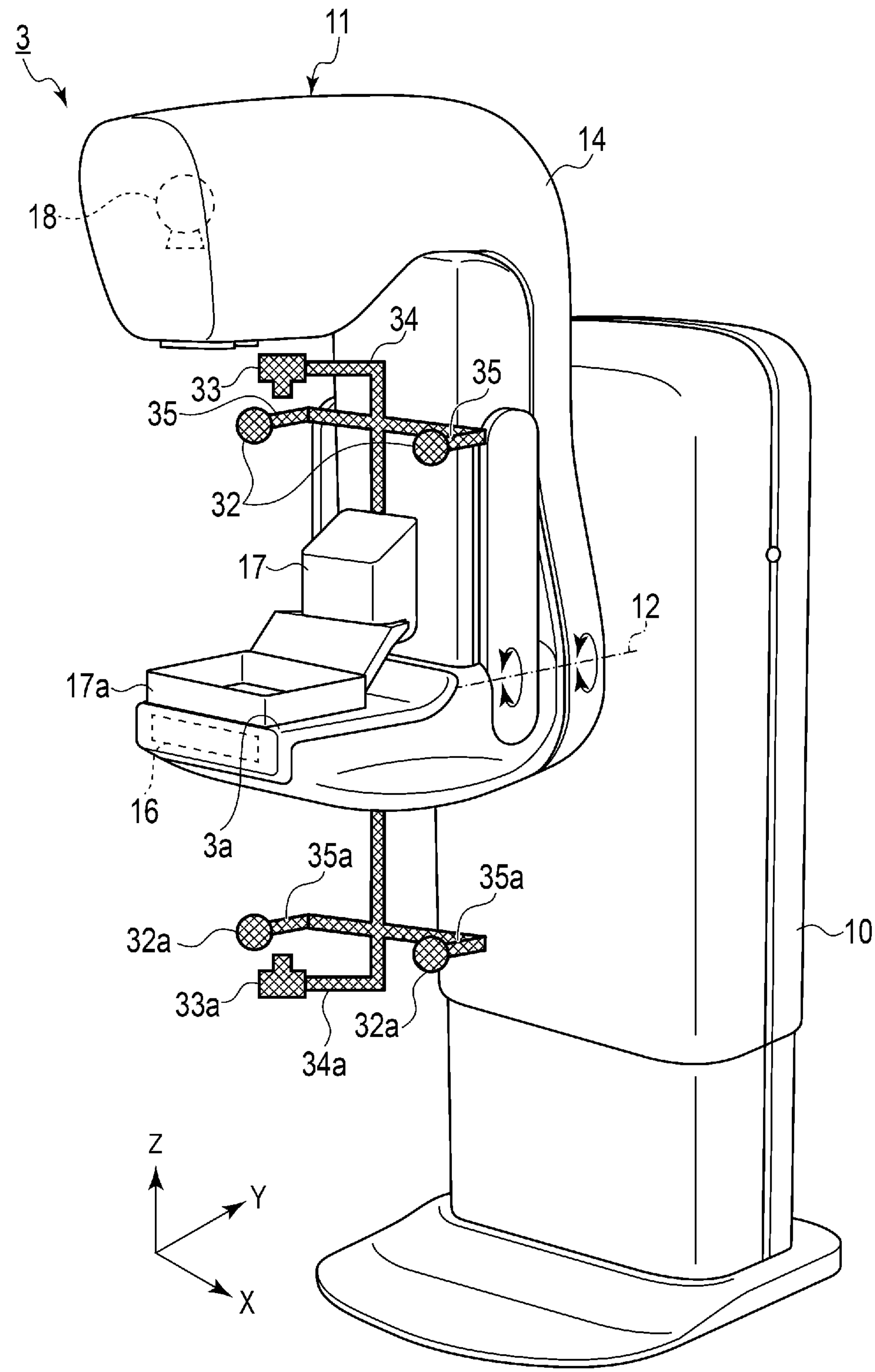
FIG. 12 is a perspective view showing an example of an outer appearance of X-ray imaging equipment according to the fourth embodiment.
Figure 13:
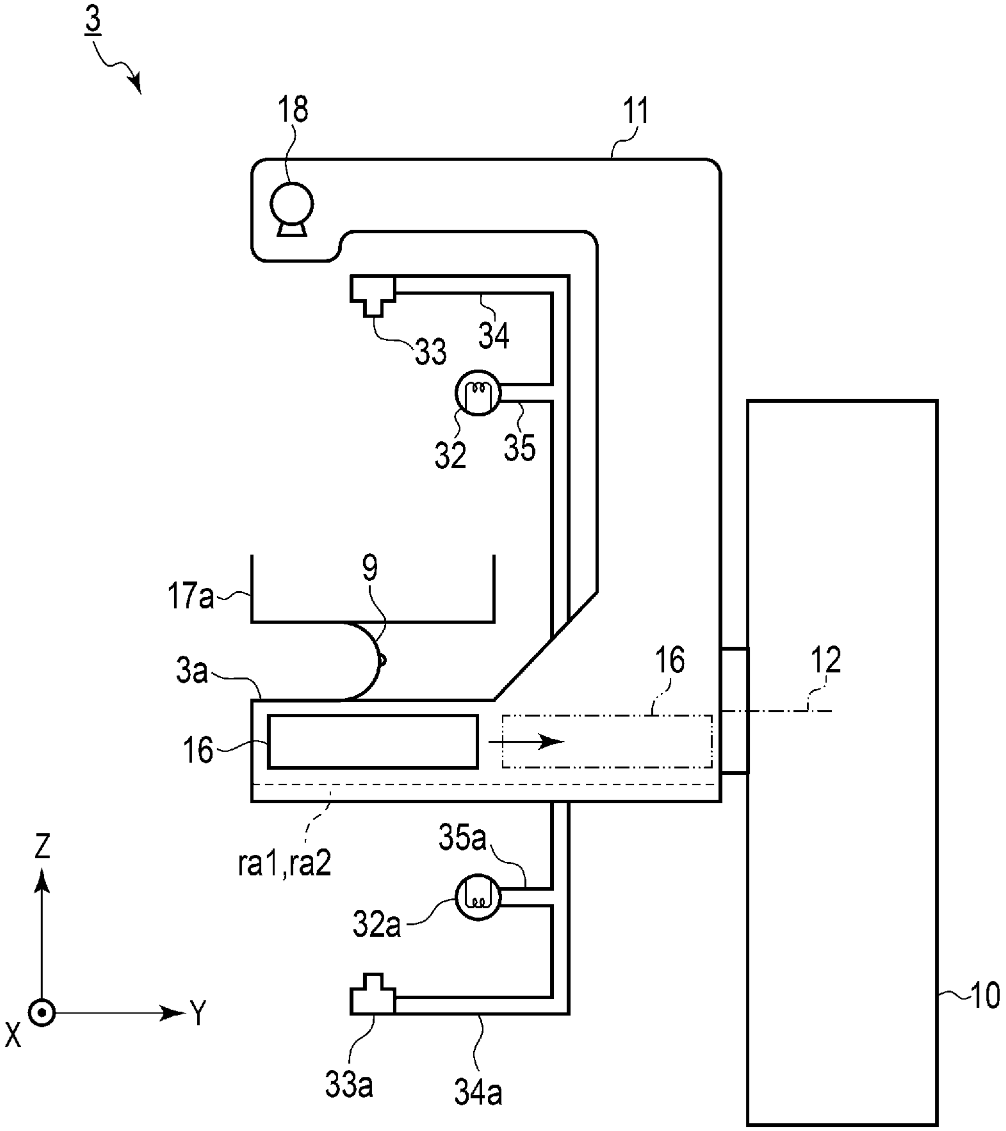
FIG. 13 is a schematic diagram for illustrating a configuration example of the X-ray imaging equipment according to the fourth embodiment.

FIG. 11 is a block diagram showing a configuration of an X-ray diagnostic apparatus according to the fourth embodiment, and FIG. 12 is a perspective view showing an example of an outer appearance of X-ray imaging equipment in the X-ray diagnostic apparatus. FIG. 13 is a schematic diagram showing a configuration of the X-ray imaging equipment.

The X-ray imaging equipment 3 further includes, in addition to the above-described configuration, a signal generator 31*a*, flash lamps 32*a*, and an infrared camera 33*a*. The flash lamps 32 and the infrared camera 33 with the above-described configuration are examples of a first flash lamp and a first infrared camera, respectively. The flash lamps 32*a* and the infrared camera 33*a* are examples of the second flash lamp and the second infrared camera, respectively. The flash lamps 32 and 32*a*, the infrared cameras 33 and 33*a*, and the image generation circuitry 25 are other examples of the first imaging unit.

The signal generator 31*a* is controlled by the processing circuitry 26, generates a periodic signal, and sends it to the flash lamps 32*a*. The signal generator 31*a* may be implemented on the computer apparatus 5.

In response to the periodic signal that has been sent, the flash lamps 32*a* irradiate the subject 9 with infrared rays diagonally from below the subject. For the infrared rays, near-infrared rays, mid-infrared rays, far-infrared rays, or a combination of the neighboring rays may be used.

The infrared camera 33*a* continuously images the subject 9 periodically irradiated with infrared rays from below the subject, and sends a plurality of items of thermographic image data obtained through the imaging to the computer apparatus 5.

The image generation circuitry 25 obtains three-dimensional thermographic image data based on a plurality of items of thermographic image data sent from the infrared camera 33 arranged above the compression plate 17*a* and a plurality of items of thermographic image data sent from the infrared camera 33*a* arranged below the supporting base 3*a*.

The image generation circuitry 25 obtains, for example, first three-dimensional thermographic image data based on a plurality of items of thermographic image data sent from the infrared camera 33 which has imaged the subject 9 irradiated with infrared rays from above.

Also, the image generation circuitry 25 obtains, for example, second three-dimensional thermographic image data based on a plurality of items of thermographic image data sent from the infrared camera 33*a* which has imaged the subject 9 irradiated with infrared rays from below.

Moreover, the image generation circuitry 25 acquires, for example, third three-dimensional thermographic image data by merging the first three-dimensional thermographic image data with the second three-dimensional thermographic image data. The third three-dimensional thermographic image data is synthesized three-dimensional thermographic image data, and has an improved resolution compared to the three-dimensional thermographic image data acquired in the first embodiment. Here, the image generation circuitry 25 may merge the first three-dimensional thermographic image data with the second three-dimensional thermographic image data by applying weighting according to the depth from the infrared irradiation surface of the subject 9.

On the other hand, the supporting base 3*a* is formed of a material that allows infrared rays to pass therethrough, and a breast of the subject 9 is mounted thereon. Examples of such a material that can be suitably used include an acrylic resin and glass, which allow infrared rays to pass therethrough. It is preferable that the supporting base 3*a* be formed of a same material as the material of the compression plate 17*a*, from the viewpoint that it is preferable to obtain the first and second three-dimensional thermographic image data under the same measurement environment. The supporting base 3*a* is an example of a mounting base on which the subject 9 is mounted and which allows infrared rays to pass therethrough. Rails ra1 and ra2 are provided below the supporting base 3*a*.

The rails ra1 and ra2 have a longitudinal direction approximately parallel to a longitudinal direction of the axial portion 12 around which the C-arm 11 rotates, and support the X-ray detector 16 so as to interpose it from side surfaces. Also, the rails ra1 and ra2 movably support the X-ray detector 16 from a region between the lower-side flash lamps 32*a* and the infrared camera 33*a* and the breast.

The imaging control circuitry 24 causes the X-ray detector 16 to retract from a region between the lower-side flash lamps 32*a* and the infrared camera 33*a* and the breast of the subject 9 prior to starting of imaging using the lower-side flash lamps 32*a* and the infrared camera 33*a*. The grid positioned between the X-ray detector 16 and the supporting base 3*a* is retracted integrally with the X-ray detector 16. The imaging control circuitry 24 is an example of the retraction control circuitry.

The other configurations are similar to those of the first embodiment.

Figure 14:
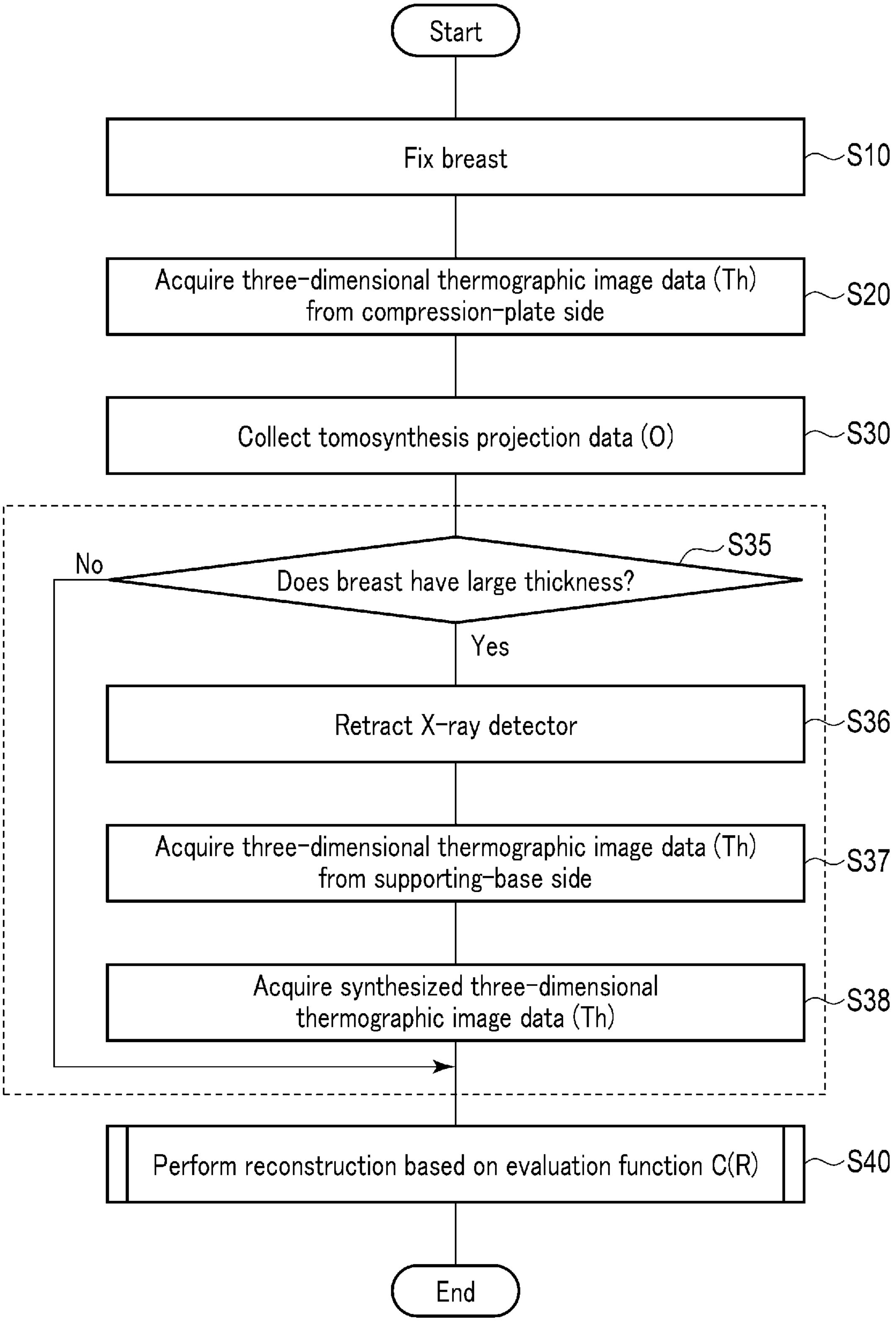
FIG. 14 is a flowchart for illustrating an operation according to the fourth embodiment.
Figure 15:
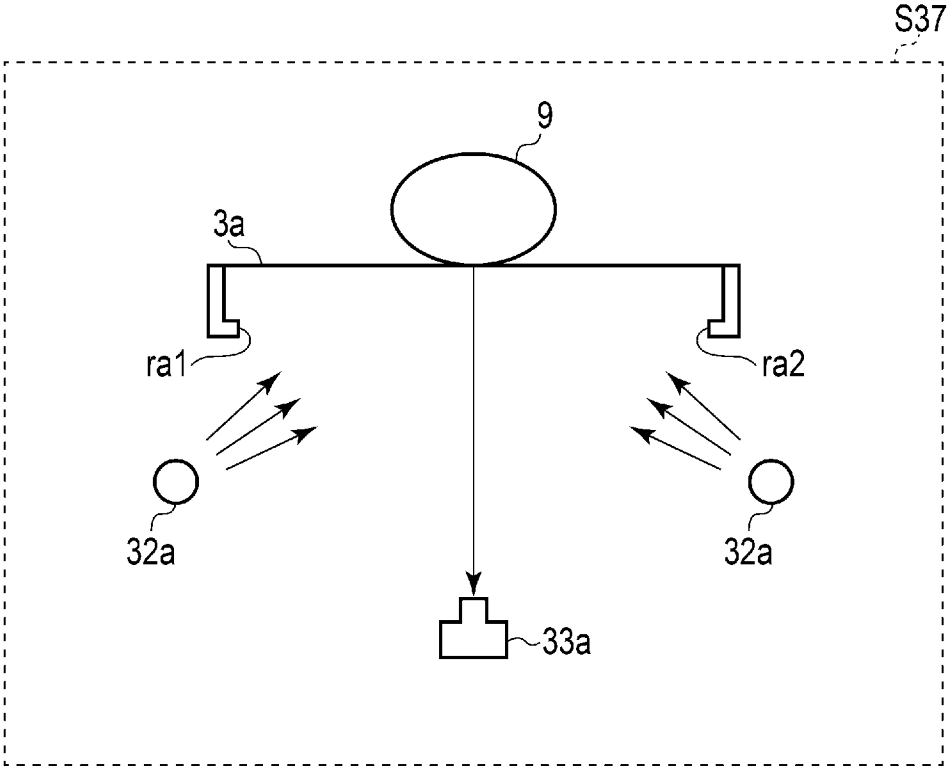
FIG. 15 is a schematic diagram for illustrating an operation at step S37 in FIG. 14.

Next, an operation of the X-ray diagnostic apparatus with the above-described configuration will be described with reference to the flowchart in FIG. 14 and the schematic diagram of FIG. 15.

First, the X-ray diagnostic apparatus 1 executes step S10, and a breast of the subject 9 is fixed onto the supporting base 3*a*, similarly to the above-described configuration.

After step S10, step S20 is executed, similarly to the above-described configuration. The image generation circuitry 25 obtains first three-dimensional thermographic image data (Th) based on a plurality of items of thermographic image data sent from the infrared camera 33 which has imaged the subject 9 irradiated with infrared rays from the side of the compression plate 17*a*.

After step S20, step S30, in which tomosynthesis imaging is performed, is executed, similarly to the above-described configuration.

After step S30, the imaging control circuitry 24 determines, at step S35, whether or not the breast to be measured has a large thickness based on, for example, a breast width of the subject 9 and a threshold value, and if it is determined that it does not, the processing shifts to step S40. On the other hand, if it is determined, at step S35, that the breast has a large thickness, the imaging control circuitry 24 shifts to step S36 to start imaging using the lower-side flash lamps 32*a* and the infrared camera 33*a*. The determination at step S35 is not necessarily performed after step S30, and may be executed at a given timing between step S10 and step S36.

At step S36, the imaging control circuitry 24 causes the X-ray detector 16 to retract along the rails ra1 and ra2 from a region between the lower-side flash lamps 32*a* and the infrared camera 33*a* and the breast of the subject 9, as shown in FIG. 13, prior to starting of imaging of the lower side.

After step S36, the X-ray diagnostic apparatus 1 performs, at step S37, imaging similar to that of step S20 from the lower side. That is, the X-ray diagnostic apparatus 1 performs imaging of the fixed breast with active thermography from the side of the supporting base 3*a*, in response to the operator's operation. In the X-ray diagnostic apparatus 1, the signal generator 31*a* generates a periodic signal and sends it to the flash lamps 32*a*. In response to the periodic signal that has been sent, the flash lamps 32*a* irradiate the breast of the subject 9 with infrared rays diagonally from below the breast via the supporting base 3*a*, as shown in FIG. 15. At this time, since the X-ray detector 16 and the grid are not positioned below the supporting base 3*a*, the lower side of the breast is irradiated with infrared rays via the supporting base 3*a*. The infrared camera 33*a* continuously images the breast of the subject 9 periodically irradiated with infrared rays, and sends a plurality of items of thermographic image data obtained through the imaging to the computer apparatus 5. The image generation circuitry 25 of the computer apparatus 5 performs a lock-in process based on a plurality of items of thermographic image data that have been sent, and obtains second three-dimensional thermographic image data (Th). Thereafter, the image generation circuitry 25 saves the obtained second three-dimensional thermographic image data in the memory 22.

After step S37, the image generation circuitry 25 merges, at step S38, first three-dimensional thermographic image data obtained at step S20 with second three-dimensional thermographic image data obtained at step S37. At this time, the image generation circuitry 25 may merge the first three-dimensional thermographic image data with the second three-dimensional thermographic image data by applying weighting according to the depth from the infrared irradiation surface of the subject 9. Specifically, weighting that adds a lower weight to a greater depth from an irradiation surface, which is the surface of the breast, may be used. In the case of the first three-dimensional thermographic image data, weighting that adds a lower weight w1 to a position farther from the compression plate 17*a* and closer to the supporting base 3*a* between the compression plate 17*a* and the supporting base 3*a* is used. In the case of the second three-dimensional thermographic image data, weighting that adds a lower weight w2 to a position closer to the compression plate 17*a* and farther from the supporting base 3*a* between the compression plate 17*a* and the supporting base 3*a* is used. In the vicinity of the center between the compression plate 17*a* and the supporting base 3*a*, the weights w1 and w2 of the first and second three-dimensional thermographic image data become equal. The sum of the weights w1 and w2 may be 1, with each of the weights w1 and w2 falling in the range from equal to or greater than 0 and equal to or smaller than 1 ($0 \le w1 \le 1$, $0 \le w2 \le 1$, $w1+w2=1$). Also, the weights w1 and w2 may be expressed as, for example, $w1=d1/da$ and $w2=d2/da$, where da is the distance between the compression plate 17*a* and the supporting base 3*a*, d1 is the depth from the irradiation surface contacting the compression plate 17*a*, and d2 is the depth from the irradiation surface contacting the supporting base 3*a*. In this case, the relationship of $da=d1+d2$ is satisfied. In these examples, the synthesized third three-dimensional thermographic image data is obtained based on the first three-dimensional thermographic image data and the second three-dimensional thermographic image data, and a weighted mean of the respective weights w1 and w2. However, the weighted mean need not necessarily be used, and the synthesized third three-dimensional thermographic image data may be obtained as a combination of an upper half of the first three-dimensional thermographic image data and a lower half of the second three-dimensional thermographic image data.

In either case, the image generation circuitry 25 saves the synthesized third three-dimensional thermographic image data in the memory 22 upon obtaining it. Thereby, the processing circuitry 26 acquires the third three-dimensional thermographic image data in the memory 22.

After step S38, the processing at step S40 and thereafter is executed, similarly to the above-described configuration.

According to the fourth embodiment, the image generation circuitry 25 obtains first three-dimensional thermographic image data based on a plurality of items of thermographic image data sent from the infrared camera 33 which has imaged the subject 9 irradiated with infrared rays from above, as described above. Also, the image generation circuitry 25 obtains second three-dimensional thermographic image data based on a plurality of items of thermographic image data sent from the infrared camera 33*a* which has imaged the subject 9 irradiated with infrared rays from below. Moreover, the image generation circuitry 25 acquires third three-dimensional thermographic image data by merging the first three-dimensional thermographic image data with the second three-dimensional thermographic image data. Accordingly, with the configuration of merging the first three-dimensional thermographic image data obtained by imaging from above and the second three-dimensional thermographic image data obtained by imaging from below, it is possible to improve the resolution of three-dimensional thermographic image data, in addition to the effects of the first embodiment.

Moreover, according to the fourth embodiment, the image generation circuitry 25 may merge the first three-dimensional thermographic image data with the second three-dimensional thermographic image data by applying weighting according to the depth from the infrared irradiation surface of the subject 9. In this case, it is possible to improve the resolution according to the depth from the irradiation surface, in addition to the above-described effects.

Furthermore, according to the fourth embodiment, the supporting base 3*a*, on which the subject 9 is mounted, allows infrared rays to pass therethrough. In this case, since infrared rays applied from below pass through the breast of the subject 9, it is possible to realize imaging with active thermography from below, in addition to the above-described effects.

Moreover, according to the fourth embodiment, the flash lamps 32 irradiate the subject 9 with infrared rays from above. The infrared camera 33 images the subject 9 irradiated with infrared rays by the flash lamps 32, and sends a plurality of items of thermographic image data. On the other hand, the flash lamps 32*a* irradiate the subject 9 with infrared rays from below. The infrared camera 33*a* images the subject 9 irradiated with infrared rays by the flash lamps 32*a*, and sends a plurality of items of thermographic image data. The image generation circuitry 25 obtains three-dimensional thermographic image data based on a plurality of items of thermographic image data sent from the infrared camera 33 and a plurality of items of thermographic image data sent from the infrared camera 33*a*. Accordingly, it is possible to realize imaging with active thermography from diametrically opposite imaging directions.

Furthermore, according to the fourth embodiment, the imaging control circuitry 24 causes the X-ray detector 16 to retract from a region between the lower-side flash lamps 32*a* and the infrared camera 33*a* and the breast of the subject 9 prior to starting of imaging using the lower-side flash lamps 32*a* and the infrared camera 33*a*. Accordingly, with the configuration of causing the X-ray detector 16 configured to shield infrared rays to retract prior to irradiation of the subject 9 with infrared rays from below, it is possible to realize imaging with active thermography from below, in addition to the above-described effects.

Moreover, according to the fourth embodiment, the rails ra1 and ra2 movably support the X-ray detector 16 from a region between the lower-side flash lamps 32*a* and the infrared camera 33*a* and the breast. Accordingly, with the X-ray detector 16 moving along the rails ra1 and ra2 at the time of the retraction of the X-ray detector 16, it is possible to avoid interference with the subject 9, etc. and maintain safety, in addition to the above-described effects.

<Modifications>

In the fourth embodiment, the image generation circuitry 25 merges first three-dimensional thermographic image data with second three-dimensional thermographic image data; however, the configuration is not limited thereto. For example, the first acquisition function 261 of the processing circuitry 26 may acquire the third three-dimensional thermographic image data by merging the first and second three-dimensional thermographic image data obtained by the image generation circuitry 25. That is, the first acquisition function 261 may acquire third three-dimensional thermographic image data by merging the first three-dimensional thermographic image data obtained by imaging the subject 9 irradiated with infrared rays from above and the second three-dimensional thermographic image data obtained by imaging the subject 9 irradiated with infrared rays from below. In this case, the first acquisition function 261 may merge the first three-dimensional thermographic image data with the second three-dimensional thermographic image data by applying weighting according to the depth from the infrared irradiation surface of the subject 9. With such modification, it is possible to obtain similar effects as can be obtained by the fourth embodiment.

Alternatively, the image generation circuitry 25 may directly obtain third three-dimensional thermographic image data based on a plurality of items of thermographic image data sent from an upper-side infrared camera 33 and a plurality of items of thermographic image data sent from a lower-side infrared camera 33*a*. That is, the image generation circuitry 25 may acquire third three-dimensional thermographic image data based on a plurality of items of thermographic image data sent from the infrared cameras 33 and 33*a*, without acquiring the first and second three-dimensional thermographic image data. In this case, the image generation circuitry 25 may generate third three-dimensional thermographic image data based on a plurality of items of thermographic image data from the infrared cameras 33 and 33*a* by applying weighting according to the depth from the infrared irradiation surface of the subject 9. According to such a modification, since generation of three-dimensional thermographic image data needs to be performed only once, it is possible to reduce the burden in image processing of acquiring first three-dimensional thermographic image data and second three-dimensional thermographic image data and merging them, in addition to the effects of the fourth embodiment.

Fifth Embodiment

A fifth embodiment is designed as a combination of the second and fourth embodiments. That is, the fifth embodiment is designed to improve the resolution of the lower side of the three-dimensional thermographic image data by acquiring and merging a plurality of items of three-dimensional thermographic image data captured by imaging the subject 9 into which a medication that generates heat through infrared irradiation has been administered from diametrically opposite imaging directions.

In accordance therewith, the X-ray diagnostic apparatus 1 has a configuration similar to that of the second embodiment, in addition to the configuration of the fourth embodiment shown in FIGS. 11 to 13. For example, the X-ray diagnostic apparatus 1 acquires three-dimensional thermographic image data relating to the subject 9 into which a medication that generates heat through infrared irradiation has been administered, in the configurations shown in FIGS. 11 to 13. The configuration relating to the parameter α is similar to that of the second embodiment.

The other configurations are similar to those of the second and fourth embodiments.

Figure 16:
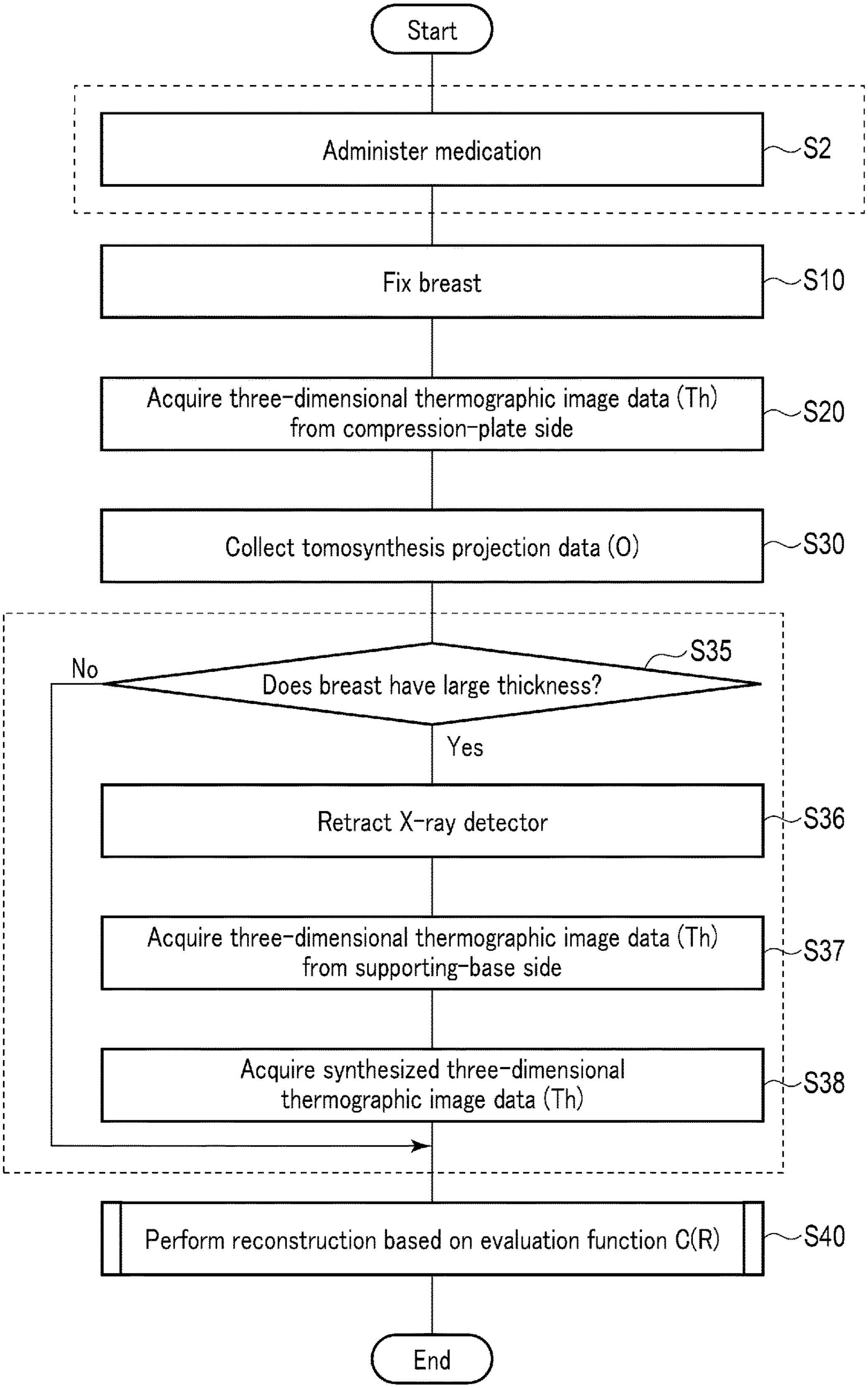
FIG. 16 is a flowchart for illustrating an operation according to a fifth embodiment.

Next, an operation of the X-ray diagnostic apparatus with the above-described configuration will be described with reference to the flowchart in FIG. 16.

First, at step S2, the medication that generates heat through infrared irradiation is administered into the subject 9, similarly to the second embodiment. Also, the processing circuitry 26 sets the parameter α to have a greater value in the case where a medication is administered than in the case where such a medication is not used, similarly to the second embodiment.

After step S2, steps S10 to S30 and S35 to S38 are executed, similarly to the fourth embodiment. Thereby, tomosynthesis projection data (O) and synthesized three-dimensional thermographic image data (Th) are acquired. The synthesized three-dimensional thermographic image data has an improved resolution, as described above.

After step S38, step S40 is executed, similarly to the second embodiment. That is, of step S40, at step S43 at which the value of partial differentiation is calculated, the rate at which information of the synthesized three-dimensional thermographic image data (Th) is introduced increases in accordance with the value of the parameter α. As a result, accumulation of the medication is reflected in the reconstructed tomosynthesis image data (R).

According to the fifth embodiment described above, with the configuration of executing steps S2 and S40 relating to the second embodiment and steps S20 and S35-S38 relating to the fourth embodiment, it is possible to obtain the effects of both of the second and fourth embodiments. For example, with the configuration of merging three-dimensional thermographic image data obtained by imaging the subject 9 into which a medication that generates heat through infrared irradiation is imaged from two imaging directions, it is possible to achieve an improved resolution of three-dimensional thermographic image data with an emphasis on the tumor. Accordingly, it is possible to reconstruct tomosynthesis images using high-resolution three-dimensional thermographic image data with an emphasis on the tumor.

<Modifications>

The fifth embodiment is a combination of the second and fourth embodiments; however, the configuration is not limited thereto. For example, the second embodiment may be combined with the modification of the fourth embodiment. Similarly, the modification of the second embodiment may be combined with the fourth embodiment and its modification.

Sixth Embodiment

The sixth embodiment is designed as a combination of the third and fourth embodiments. That is, it is designed to reduce the examination time through parallel execution of two types of imaging, and to improve the resolution through synthesis of two items of three-dimensional thermographic image data.

In accordance therewith, the X-ray diagnostic apparatus 1 has a configuration similar to that of the third embodiment, in addition to the configuration of the fourth embodiment shown in FIGS. 11 to 13. For example, the imaging control circuitry 24 of the X-ray diagnostic apparatus 1 causes imaging with infrared irradiation from above and tomosynthesis imaging to be performed in parallel.

The other configurations are similar to those of the third and fourth embodiments.

Figure 17:
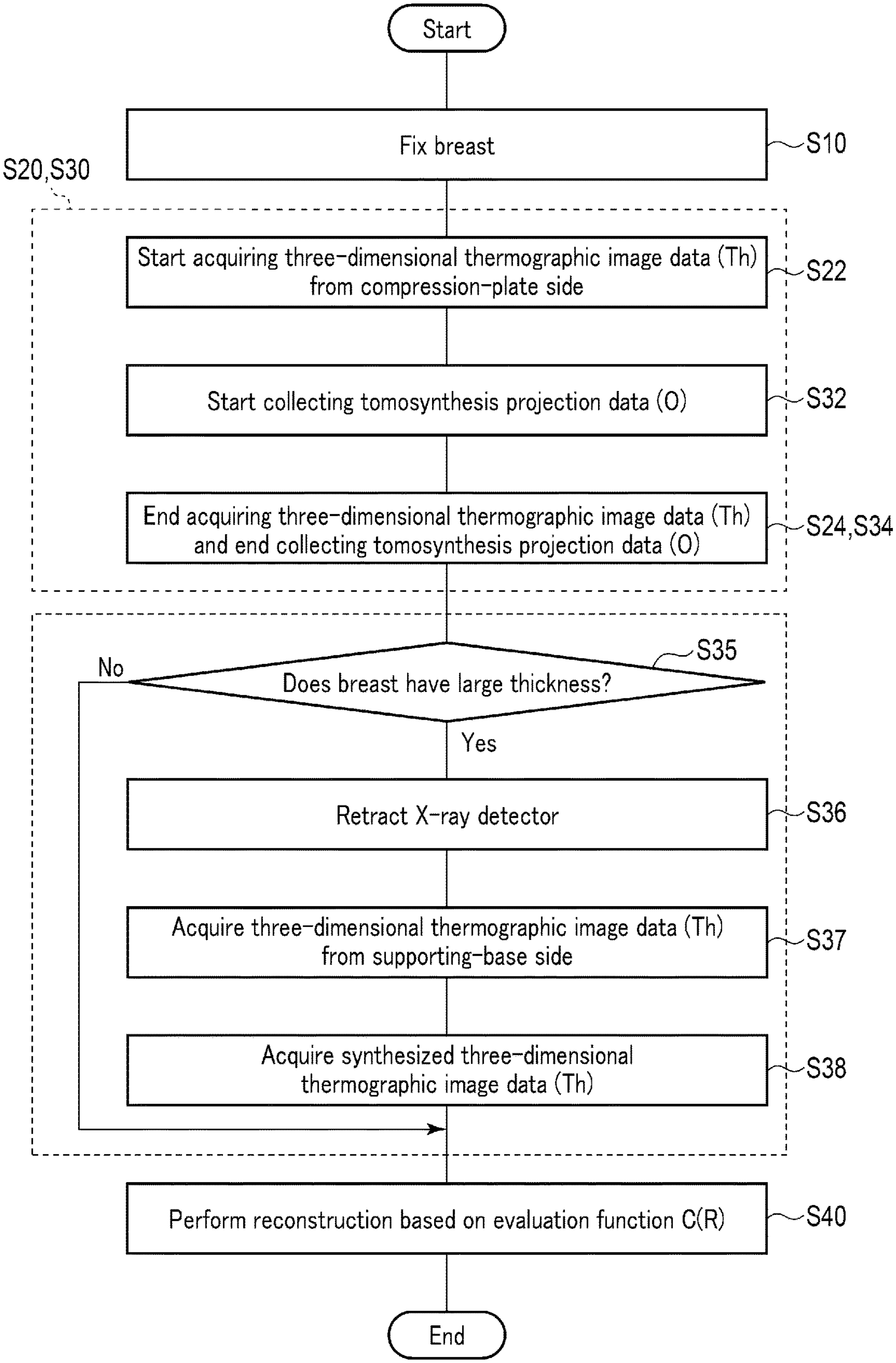
FIG. 17 is a flowchart for illustrating an operation according to a sixth embodiment.

Next, an operation of the X-ray diagnostic apparatus with the above-described configuration will be described with reference to the flowchart in FIG. 17.

First, after step S10 is executed, steps S20 and S30 are executed in parallel, similarly to the third embodiment. Thereby, three-dimensional thermographic image data (Th) captured from above is acquired, and tomosynthesis projection data (O) is collected. Accordingly, the examination time is reduced through parallel execution of the two types of imaging.

After steps S20 and S30, steps S35 to S38 are executed, similarly to the fourth embodiment. Thereby, synthesized three-dimensional thermographic image data (Th) is obtained. The synthesized three-dimensional thermographic image data has an improved resolution, as described above.

After step S38, the processing at step S40 and thereafter is executed, similarly to the fourth embodiment.

According to the sixth embodiment described above, with the configuration including execution of steps S20 and S30 relating to the third embodiment in parallel and execution of steps S35 to S38 relating to the fourth embodiment, it is possible to obtain the effects of both of the third and fourth embodiments. With the configuration of, for example, executing two types of imaging in parallel and merging two items of three-dimensional thermographic image data, it is possible to reduce the examination time and to improve the resolution of the three-dimensional thermographic image data.

<Modifications>

The sixth embodiment is a combination of the third and fourth embodiments; however, the configuration is not limited thereto. For example, the third embodiment may be combined with a modification of the fourth embodiment. Similarly, a modification of the third embodiment may be combined with the fourth embodiment and its modification.

According to at least one of the embodiments described above, it is possible to increase the resolution in the depth direction without widening the range of irradiation angles in tomosynthesis imaging.

The term "processor" used herein means, for example, circuitry such as a central processing unit (CPU), a graphics processing unit (GPU), or circuitry such as an application-specific integrated circuit (ASIC), a programmable logic device (e.g., a simple programmable logic device (SPLD), a complex programmable logic device (CPLD), etc.), or a field-programmable gate array (FPGA), etc. The processor reads programs stored in a memory and executes them to realize the intended functions. If the processor is, for example, a CPU, the processor reads and executes programs stored in storage circuitry to realize the functions. If the processor is, for example, an ASIC, the functions are directly incorporated into the circuitry of the processor as logic circuitry, instead of the programs being stored in the storage circuitry. Each processor in the present embodiment is not limited to a single circuitry-type processor, and multiple independent circuits may be combined and integrated as a single processor to realize the intended functions. Furthermore, multiple components or features as given in FIGS. 1 and 11 may be integrated as a single processor to realize the respective functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray diagnostic apparatus, comprising:

processing circuitry configured to:

acquire three-dimensional thermographic image data by imaging a breast of a subject irradiated with infrared rays;

acquire a plurality of items of two-dimensional projection X-ray image data by imaging the breast of the subject with tomosynthesis; and execute reconstruction based on the plurality of items of two-dimensional projection X-ray image data and the three-dimensional thermographic image data, a first imaging unit configured to image the breast and to obtain the three-dimensional thermographic image data;

a second imaging unit configured to image the breast with tomosynthesis and to obtain the plurality of items of two-dimensional projection X-ray image data; and control circuitry configured to cause the imaging with the first imaging unit and the tomosynthesis imaging with the second imaging unit to be executed in parallel, wherein the processing circuitry is further configured to iteratively execute the reconstruction to reduce errors between three-dimensional tomosynthesis X-ray image data obtained by the execution of the reconstruction and three-dimensional tomosynthesis model X-ray image data corresponding to the three-dimensional thermographic image data, the first imaging unit includes a first flash lamp configured to irradiate the breast with the infrared rays from above the breast;

a first infrared camera configured to image the breast irradiated with the infrared rays by the first flash lamp and to send a plurality of items of first thermographic image data:

a second flash lamp configured to irradiate the breast with the infrared rays from below the breast:

a second infrared camera configured to image the breast irradiated with the infrared rays by the second flash lamp and to send a plurality of items of second thermographic image data; and image generation circuitry configured to obtain a first type of three-dimensional thermographic image data based on the plurality of items of first thermographic image data sent from the first infrared camera, obtain a second type of three-dimensional thermographic image data based on the plurality of items of second thermographic image data sent from the second infrared camera, and obtain a third type of three-dimensional thermographic image data based on the first type of three-dimensional thermographic image data and the second type of three-dimensional thermographic image data, the second imaging unit includes an X-ray detector used in the tomosynthesis imaging, the control circuitry is configured to determine whether a thickness of the breast exceeds a threshold value, after causing the first imaging unit to execute the imaging with the first flash lamp and the first infrared camera, and to cause the first imaging unit to start the imaging with the second flash lamp and the second infrared camera if the thickness of the breast exceeds the threshold value, and the three-dimensional thermographic image data is the first type of three-dimensional thermographic image data if the thickness of the breast is less than or equal to the threshold value, and the three-dimensional thermographic image data is the third type of three-dimensional thermographic image data if the thickness of the breast exceeds the threshold value.

2. The X-ray diagnostic apparatus according to claim 1, further comprising:

a mounting base on which the subject is mounted and which allows the infrared rays to pass therethrough; and a compression plate formed of a material same as a material of the mounting base.

3. The X-ray diagnostic apparatus according to claim 1, further comprising retraction control circuitry, wherein the retraction control circuitry is configured to cause the X-ray detector to retract from a region between the second flash lamp and the second infrared camera and the subject prior to starting of the imaging using the second flash lamp and the second infrared camera.

4. The X-ray diagnostic apparatus according to claim 3, further comprising:

rails configured to support the X-ray detector to allow movement of the X-ray detector from the region.

5. The X-ray diagnostic apparatus according to claim 1, wherein the processing circuitry is further configured to generate the three-dimensional tomosynthesis model X-ray image data by converting a size and a pixel value range of the three-dimensional thermographic image data into a size and a pixel value of the three-dimensional tomosynthesis X-ray image data.

6. The X-ray diagnostic apparatus according to claim 1, wherein the processing circuitry is further configured to iteratively execute the reconstruction based on an evaluation function, the evaluation function including: (1) a term relating to a squared error between a plurality of items of projection data obtained by a forward projection of the three-dimensional tomosynthesis X-ray image data and the plurality of items of projection data acquired by imaging the subject with tomosynthesis; and (2) a term relating to a multiplication by a parameter of a squared error between the three-dimensional tomosynthesis X-ray image data obtained by the execution of the reconstruction and the three-dimensional tomosynthesis model X-ray image data corresponding to the three-dimensional thermographic image data.

7. The X-ray diagnostic apparatus according to claim 6, wherein the processing circuitry is further configured to partially differentiate the evaluation function with respect to the three-dimensional tomosynthesis X-ray image data, and update the three-dimensional tomosynthesis X-ray image data based on a result of the partial differentiation.

8. The X-ray diagnostic apparatus according to claim 7, wherein the processing circuitry is further configured to iterate an update loop until an exit condition is satisfied, the update loop including obtaining a result of the partial differentiation of the evaluation function with respect to the three-dimensional tomosynthesis X-ray image data and updating the three-dimensional tomosynthesis X-ray image data.

9. The X-ray diagnostic apparatus according to claim 8, wherein the exit condition is satisfied if a difference between the three-dimensional tomosynthesis X-ray image data prior to the update and the updated three-dimensional tomosynthesis X-ray image data has fallen below a threshold value, or if a number of iterations of the update loop has reached a maximum number.

10. The X-ray diagnostic apparatus according to claim 7, wherein the result of the partial differentiation is a sum of first tomosynthesis error image data and second tomosynthesis error image data, the first tomosynthesis error image data being obtained by a back projection of an error between the plurality of items of projection data obtained by the forward projection and the plurality of items of projection data acquired by imaging the subject with tomosynthesis, the second tomosynthesis error image data being obtained by multiplying, by the parameter, an error between the three-dimensional tomosynthesis X-ray image data and the three-dimensional tomosynthesis model X-ray image data, and the parameter used in the multiplication by the parameter indicates a rate at which an error relating to the three-dimensional thermographic image data is introduced.

11. The X-ray diagnostic apparatus according to claim 10, wherein the parameter has a greater value in the case where a medication that generates heat through infrared irradiation is administered into the subject than in the case where the medication is not administered.

12. The X-ray diagnostic apparatus according to claim 1, wherein the processing circuitry is further configured to acquire the three-dimensional thermographic image data relating to the subject into which a medication that generates heat through infrared irradiation has been administered.

13. The X-ray diagnostic apparatus according to claim 1, wherein the processing circuitry is further configured to acquire the three-dimensional thermographic image data by merging first three-dimensional thermographic image data obtained by imaging the subject irradiated with the infrared rays from above and second three-dimensional thermographic image data obtained by imaging the subject irradiated with the infrared rays from below.

14. The X-ray diagnostic apparatus according to claim 13, wherein the processing circuitry is further configured to merge the first three-dimensional thermographic image data with the second three-dimensional thermographic image data by applying weighting according to a depth from a surface of the irradiation of the subject with the infrared rays.

15. An X-ray diagnostic method, comprising:

acquiring three-dimensional thermographic image data by imaging a breast of a subject irradiated with infrared rays, wherein a first imaging unit configured to image the breast and to obtain the three-dimensional thermographic image data;

acquiring a plurality of items of two-dimensional projection X-ray image data by imaging the breast of the subject with tomosynthesis, wherein a second imaging unit configured to image the breast with tomosynthesis and to obtain the plurality of items of two-dimensional projection X-ray image data; and executing reconstruction based on the plurality of items of two-dimensional projection X-ray image data and the three-dimensional thermographic image data, wherein control circuitry is configured to cause the imaging with the first imaging unit and the tomosynthesis imaging with the second imaging unit to be executed in parallel, the method further comprises iteratively executing the reconstruction to reduce errors between three-dimensional tomosynthesis X-ray image data obtained by the execution of the reconstruction and three-dimensional tomosynthesis model X-ray image data corresponding to the three-dimensional thermographic image data, the first imaging unit includes a first flash lamp configured to irradiate the breast with the infrared rays from above the breast;

a first infrared camera configured to image the breast irradiated with the infrared rays by the first flash lamp and to send a plurality of items of first thermographic image data;

a second flash lamp configured to irradiate the breast with the infrared rays from below the breast;

a second infrared camera configured to image the breast irradiated with the infrared rays by the second flash lamp and to send a plurality of items of second thermographic image data; and image generation circuitry configured to obtain a first type of three-dimensional thermographic image data based on the plurality of items of first thermographic image data sent from the first infrared camera, obtain a second type of three-dimensional thermographic image data based on the plurality of items of second thermographic image data sent from the second infrared camera, and obtain a third type of three-dimensional thermographic image data based on the first type of three-dimensional thermographic image data and the second type of three-dimensional thermographic image data, the second imaging unit includes an X-ray detector used in the tomosynthesis imaging, the control circuitry is further configured to determine whether a thickness of the breast exceeds a threshold value, after causing the first imaging unit to execute the imaging with the first flash lamp and the first infrared camera, and to cause the first imaging unit to start the imaging with the second flash lamp and the second infrared camera if the thickness of the breast exceeds the threshold value, and the three-dimensional thermographic image data is the first type of three-dimensional thermographic image data if the thickness of the breast is less than or equal to the threshold value, and the three-dimensional thermographic image data is the third type of three-dimensional thermographic image data if the thickness of the breast exceeds the threshold value.

* * * * *